(12) United States Patent
Bushweller et al.

(10) Patent No.: US 10,562,890 B2
(45) Date of Patent: Feb. 18, 2020

(54) CANCER THERAPEUTICS

(71) Applicant: UNIVERSITY OF VIRGINIA PATENT FOUNDATION, Charlottesville, VA (US)

(72) Inventors: John H. Bushweller, Crozet, VA (US); Anuradha Illendula, Crozet, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 0 days.

(21) Appl. No.: 15/503,188

(22) PCT Filed: Aug. 13, 2015

(86) PCT No.: PCT/US2015/045110
§ 371 (c)(1),
(2) Date: Feb. 10, 2017

(87) PCT Pub. No.: WO2016/025744
PCT Pub. Date: Feb. 18, 2016

(65) Prior Publication Data
US 2017/0233375 A1 Aug. 17, 2017

Related U.S. Application Data

(60) Provisional application No. 62/036,693, filed on Aug. 13, 2014.

(51) Int. Cl.
| | |
|---|---|
| *A61K 31/4184* | (2006.01) |
| *A61K 31/4439* | (2006.01) |
| *A61K 31/5377* | (2006.01) |
| *C07D 235/18* | (2006.01) |
| *C07D 401/14* | (2006.01) |
| *C07D 401/04* | (2006.01) |
| *C07D 413/12* | (2006.01) |
| *C07D 413/14* | (2006.01) |
| *C07D 405/04* | (2006.01) |

(52) U.S. Cl.
CPC ......... *C07D 405/04* (2013.01); *C07D 235/18* (2013.01); *C07D 401/04* (2013.01)

(58) Field of Classification Search
CPC ............ A61K 31/4184; A61K 31/4439; A61K 31/5377; C07D 235/18; C07D 395/092; C07D 401/14; C07D 401/04; C07D 413/12; C07D 413/14
USPC ........ 514/234.5, 235.5, 394, 338; 548/306.1, 548/237.4, 124, 139
See application file for complete search history.

(56) References Cited

U.S. PATENT DOCUMENTS

| | | | |
|---|---|---|---|
| 4,492,708 A | 1/1985 | Spitzer | |
| 8,748,618 B2 | 6/2014 | Bushweller et al. | |
| 9,926,290 B2 * | 3/2018 | Bushweller .......... | C07D 401/04 |

FOREIGN PATENT DOCUMENTS

| | | | | |
|---|---|---|---|---|
| AU | 6469990 A | * | 4/1991 | ............. A01N 43/50 |
| WO | 2010/132684 A2 | | 11/2010 | |
| WO | WO-2010132684 A2 | * | 11/2010 | ........... C07D 401/04 |

OTHER PUBLICATIONS

International Search Report and Written Opinion of International Application No. PCT/US2015/045110, dated Nov. 19, 2015.

(Continued)

*Primary Examiner* — Matthew P Coughlin
*Assistant Examiner* — Sagar Patel
(74) *Attorney, Agent, or Firm* — J.A. Lindeman & Co., PLLC; Jeffrey Lindeman; Sulay Jhaveri

(57) ABSTRACT

This invention relates to compounds that bind to wild-type CBFβ and inhibit CBFβ binding to RUNX proteins. The potent compounds of the invention inhibit this protein-protein interaction at low micromolar concentrations, using allosteric mechanism to achieve inhibition, displace wild-type CBFβ from RUNX1 in cells, change occupancy of RUNX1 on target genes, and alter gene expression of RUNX1 target genes. These inhibitors show clear biological effects consistent with on-target RUNX protein activity. Pharmaceutical compositions containing a compound of the invention and a pharmaceutically acceptable carrier represent a separate embodiment of the invention. Another embodiment of the invention are methods of treating a RUNX-signaling-dependent cancer that expresses wild-type CBFβ in a subject in need thereof by administering to the subject a therapeutically effective amount of a compound of the invention. In one embodiment, the cancer is selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and/or adenocarcinoma. In another embodiment, the compounds of the invention can be used to treat a leukemia, lung cancer, ovarian cancer, and/or breast cancer.

18 Claims, 17 Drawing Sheets

(56) References Cited

OTHER PUBLICATIONS

International Preliminary Report on Patentability in International Application No. PCT/US2015/045110, dated Feb. 23, 2017.
Illendula et al., "A small-molecule inhibitor of the aberrant transcription factor CBFbeta-SMMHC delays leukemia in mice", Science, 2005, vol. 347, Issue 6223, pp. 779-784.

* cited by examiner

| Compound | Aqueous solubility with 0.25% DMSO |
|---|---|
| AI-4-88 | 1704 μM |
| AI-10-47 | 0.44 μM |
| AI-10-104 | 225 μM |
| AI-12-126 | 122 μM |
| AI-14-91 | 149 μM |

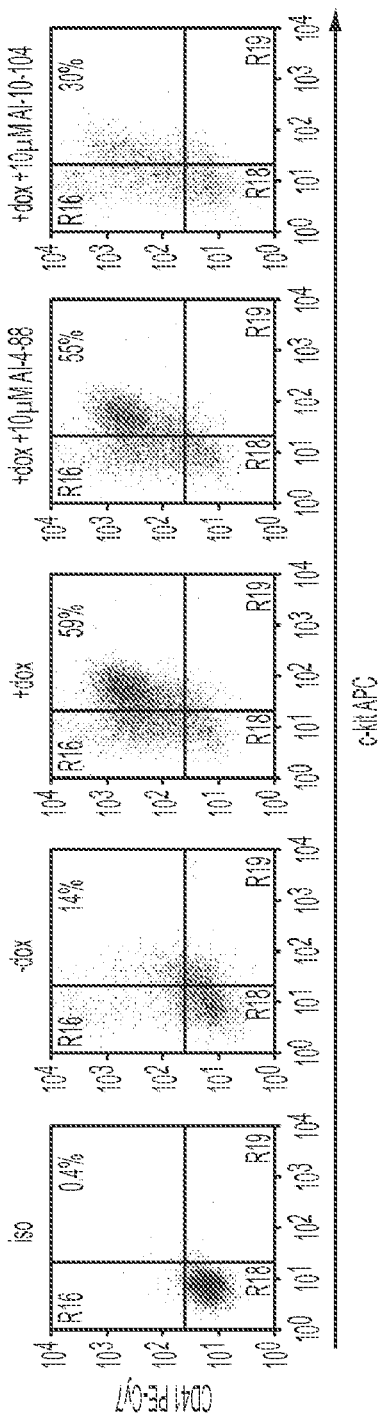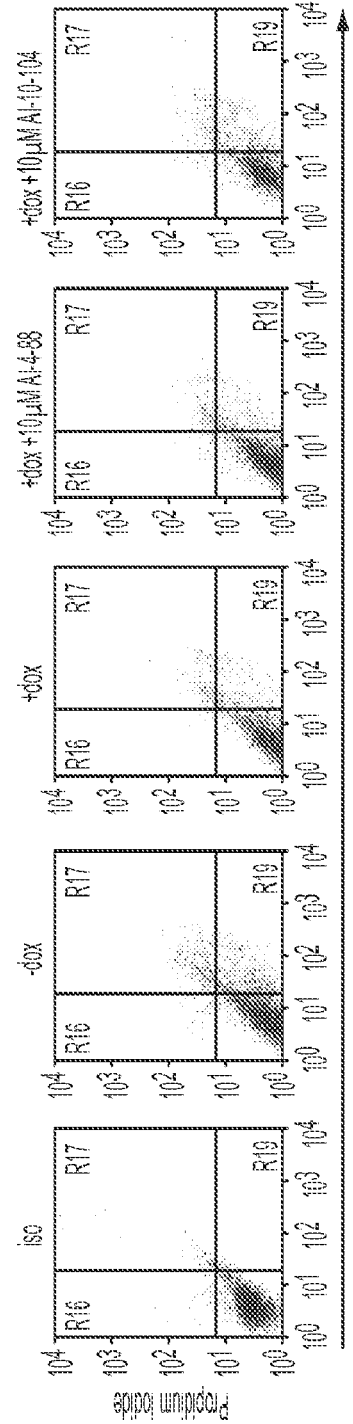
FIG. 3C
FIG. 3D

CANCER THERAPEUTICS

CROSS-REFERENCE TO RELATED APPLICATIONS

This application claims priority to U.S. Application No. 62/036,693, filed Aug. 13, 2014, which is incorporated herein by reference.

STATEMENT REGARDING FEDERALLY SPONSORED RESEARCH OR DEVELOPMENT

This invention was made with U.S. government support under Grant No. CA140398 awarded by the National Institutes of Health. The U.S. government has certain rights in the invention.

BACKGROUND OF THE INVENTION

Transcription factors represent an important as well as challenging class of proteins for development of small molecule inhibitors. Because of their function as nodes in a wide swath of signaling pathways and their well-documented importance for tumor growth and metastasis, they are particularly attractive targets for cancer therapy.

Core binding factor (CBF) is a heterodimeric transcription factor composed of a DNA-binding RUNX subunit (encoded by one of three genes: RUNX1, RUNX2, or RUNX3) and a non-DNA-binding CBFβ subunit, which increases the affinity of RUNX proteins for DNA. All three RUNX proteins as well as CBFβ have been shown to be critical regulators of specific developmental pathways. RUNX1 and CBFβ are essential for definitive hematopoiesis, where they regulate expression of genes associated with proliferation, differentiation, and survival of stem and progenitor cells. RUNX2 is essential for normal bone formation by way of transcriptional regulation of genes critical for bone development. Both RUNX1 and RUNX3 play key roles in neuronal development.

Based on their critical roles in normal development, RUNX proteins and CBFβ are targets of alteration in a number of cancers. Both RUNX1 and CBFβ undergo chromosomal translocations in a subset of acute myeloid leukemia (AML) and acute lymphocytic leukemia (ALL) patients where the corresponding fusion proteins have clearly been shown to be drivers of disease. For the fusion proteins AML1-ETO and TEL-AML1, the binding of the fusion proteins to CBFβ has been shown to be essential for transformation. RUNX1 is mutated in a subset of AML and myelodysplastic syndrome (MDS) patients.

In addition, RUNX1 has recently been implicated in a number of epithelial cancers. Recent literature also strongly implicates the RUNX family of transcription factors as playing a key role in lung cancer progression, where RUNX cooperates with GATA2 to regulate genes important in growth and survival of lung cancer cells. Altered expression of RUNX2 has also been implicated in breast and prostate cancers. Silencing of RUNX3 by DNA methylation has been linked to intestinal and lung cancers. Due to the importance of these proteins for normal development as well as in a variety of cancers, small molecules that can modulate their activity are useful tools to address function and test new therapeutic approaches.

Small molecule inhibitors of protein-protein interactions, particularly in the context of transcription factors, is still a relatively nascent field, in part due to the long and widely held belief that this class of interactions is "undruggable," i.e., targeting such interactions would have a very low likelihood of success. With an increasing number of success stories of small molecule inhibitors affecting protein-protein interactions, including transcription factors, this paradigm is clearly changing. In addition, the recent development of small molecule inhibitors of epigenetic signaling proteins, such as the BRD4 or EZH2 inhibitors, clearly indicate that small molecule modulation of transcription, in particular, is a potentially powerful approach to cancer treatment.

We recently reported in U.S. Pat. No. 8,748,618 inhibitor compounds that selectively bind to the abnormal transcription factor CBFβ-SMMHC fusion protein and inhibit its binding to the Runt domain of RUNX proteins. This binding to CBFβ-SMMHC results in delay of the type of AML that involves the chromosome inversion inv(16)(p13q22) (inv (16) leukemia). The disclosed compounds inhibited proliferation of inv(16) leukemia cells, making the compounds useful for treatment of inv(16) leukemia. There is no evidence that CBFβ-SMMHC fusion protein is present in any type of leukemia other than inv(16) leukemia or any other type of cancer.

There is thus a long-felt need in the art for compositions and methods useful for treating RUNX-signaling-dependent cancers that express wild-type CBFβ, i.e., those cancers that do not involve expression of the CBFβ-SMMHC fusion protein.

SUMMARY OF THE INVENTION

The invention relates to compounds of formula (I):

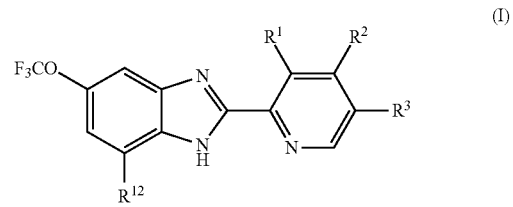

and their pharmaceutically acceptable salts. For the compounds of formula (I):
$R^1$, $R^2$ and $R^3$ are independently selected from H, $C_1$-$C_4$ alkoxy, $CO_2H$, $NR^4R^5$, $OR^6$ where $R^6$ is a group of formula (II) or of formula (IIIa-f):

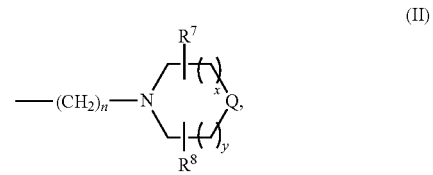

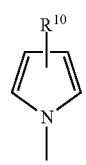

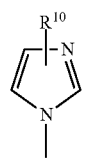

(IIIc)
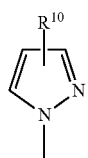

(IIId)
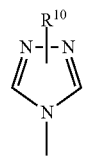

(IIIe)
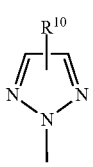

(IIIf)

and at least one of $R^1$, $R^2$ and $R^3$ is not H. $R^4$ and $R^5$ are each independently H or $C_1$-$C_3$ alkyl, or together with the nitrogen carrying them, form a pyrrolidine or a piperidine ring. The variable n ranges from 1-3; x is 0, 1 or 2; and y is 0, 1 or 2. In the group of formula (II), Q is O or N—$R^9$ and the sum of x+y≥1, or Q is a bond and the sum x+y≥2 and $R^9$ is $C_1$-$C_3$ alkyl, benzyl, —C(O)phenyl, or a $(CH_2)_nR^{11}$ where $R^{11}$ is a group of formula (IVa-f))

(IVa)
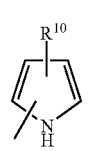

(IVb)
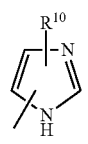

(IVc)
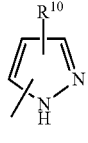

(IVd)
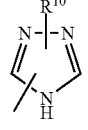

(IVe)
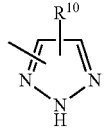

(IVf)
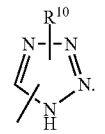

Groups $R^7$ and $R^8$ are each independently H, methyl or ethyl. Group $R^{10}$ is H, methyl, ethyl, phenyl, $CO_2H$, or tetrazole. Group $R^{12}$ is H or $(CH_2)_n$—$CO_2H$.

In second embodiment of the invention are compounds of formula (I) where $R^1$, $R^2$ and $R^3$ are independently selected from H, methoxy, ethoxy, $CO_2H$, $NR^4R^5$, or $OR^6$ where $R^6$ is a group of formula (II) or a group of formula (IIIe), and at least one of $R^1$, $R^2$ and $R^3$ is not H. $R^4$ and $R^5$ are each independently methyl or ethyl or together with the nitrogen carrying them form a pyrrolidine or a piperidine ring. n ranges from 1-3. x is 1 or 2. y is 1 or 2. Q is O or N—$R^9$ where $R^9$ is benzyl or $(CH_2)_nR^{11}$ where $R^{11}$ is a group of formula (IVd). $R^7$ and $R^8$ are both H. $R^{10}$ is methyl, phenyl or $CO_2H$. $R^{12}$ is H or $(CH_2)_n$—$CO_2H$. Within this second embodiment is a further third embodiment of the invention, where $R^1$ and $R^3$ are independently selected from H, methoxy, $CO_2H$, $NR^4R^5$, or $OR^6$ where $R^6$ is a group of formula (II); $R^2$ is H; $R^4$ and $R^5$ are each independently methyl or ethyl or together with the nitrogen carrying them form a pyrrolidine or a piperidine ring; n is 2; x is 1; y is 1; Q is O or N—$R^9$; $R^9$ is benzyl; $R^7$ and $R^8$ are both H; and Ru is H. Within the third embodiment is a further fourth embodiment of the invention where $R^1$ is H, $OCH_3$ or a group of formula (II), $R^2$ is H or $OCH_3$, and $R^3$ is H, $OCH_3$ or a group of formula (II); at least one of $R^1$, $R^2$ and $R^3$ is not H; and $R^1$ and $R^3$ are not both a group of formula (II). Within the fourth embodiment is a further fifth embodiment which is compounds where $R^2$ is H. Within the fourth embodiment is a further sixth embodiment which is compounds where $R^1$ is H or $OCH_3$. Within all these embodiments are pharmaceutically acceptable salts of the compounds.

Pharmaceutical compositions containing a compound of the invention and a pharmaceutically acceptable carrier represent a separate embodiment of the invention.

Another embodiment of the invention are methods of treating a RUNX-signaling-dependent cancer that expresses wild-type CBFβ in a subject in need thereof comprising administering to the subject a therapeutically effective amount of a compound of the invention. In one embodiment, the cancer is selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and/or adenocarcinoma. In another embodiment, the compounds of the invention can be used to treat a RUNX-signaling-dependent leukemia that expresses wild-type CBFβ, lung cancer, ovarian cancer, and/or breast cancer.

A separate embodiment of the invention are methods of treating a RUNX-signaling-dependent cancer that expresses wild-type CBFβ in a subject in need thereof comprising administering to the subject a pharmaceutical composition of the invention. In a further embodiment, the cancer is selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and/or adenocarcinoma. In another embodiment, the pharmaceutical compositions of the invention can be used to treat a RUNX-signaling-dependent leukemia that expresses wild-type CBFβ, lung cancer, ovarian cancer, and/or breast cancer.

BRIEF DESCRIPTION OF THE FIGURES

FIG. 3C. Staining of the surface markers CD41 and c-kit in cells treated with Al-4-88 and Al-10-104.

FIG. 3D. FACS histograms showing staining of Annexin V and Propidium Iodide (PI) in cells treated with compounds Al-10-104 and Al-4-88.

DETAILED DESCRIPTION

Figure 1:
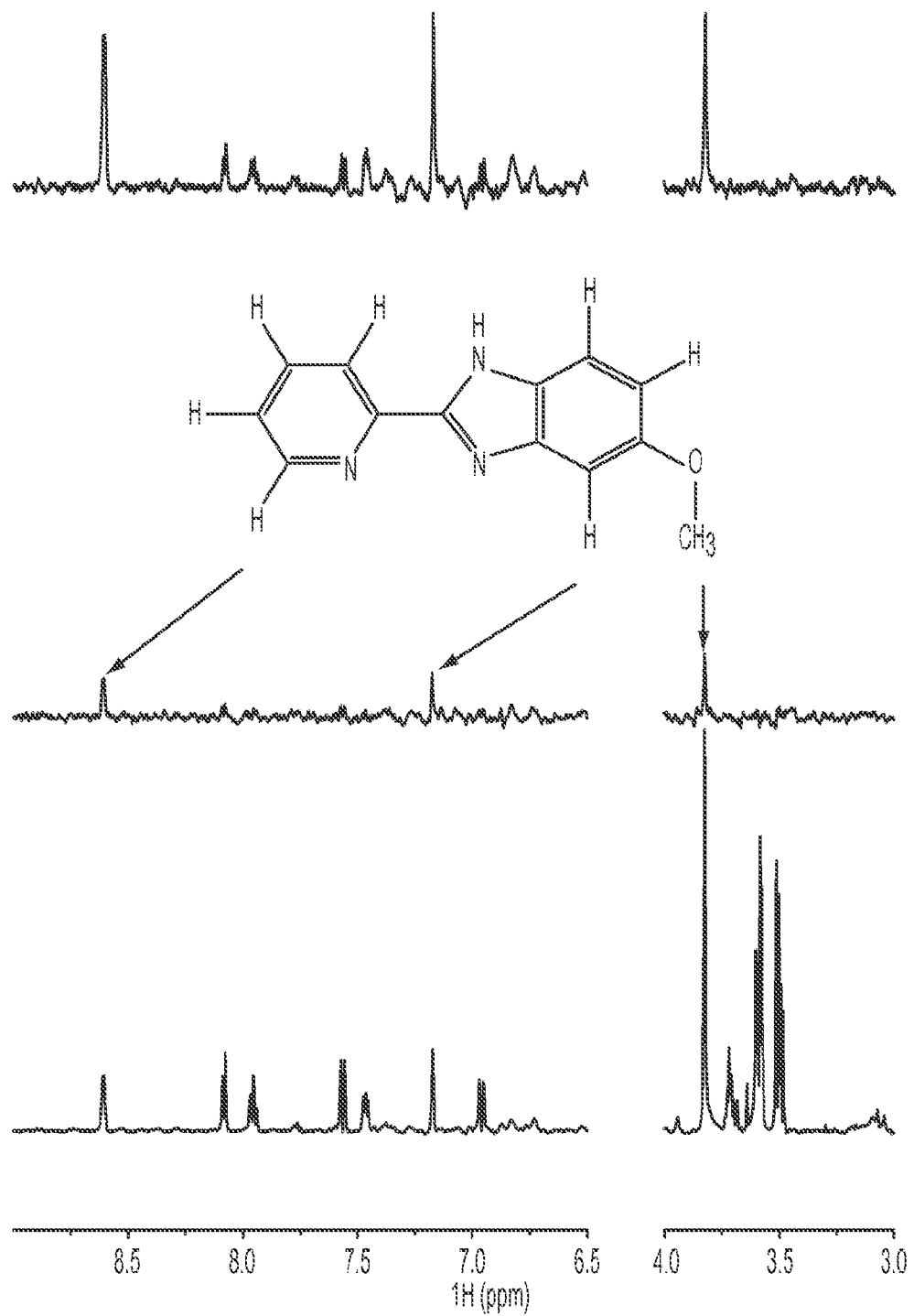
FIG. 1. Results of STD NMR analysis of Al-4-57 binding to CBFβ, discussed in Example 1.

This invention relates to compounds that bind to wild-type CBFβ and inhibit CBFβ binding to RUNX proteins. The potent compounds of the invention inhibit this protein-protein interaction at low micromolar concentrations, using allosteric mechanism to achieve inhibition, displace wild-type CBFβ from RUNX1 in cells, change occupancy of RUNX1 on target genes, and alter gene expression of RUNX1 target genes. These inhibitors show clear biological effects consistent with on-target RUNX protein activity.

The invention relates to compounds of formula (I):

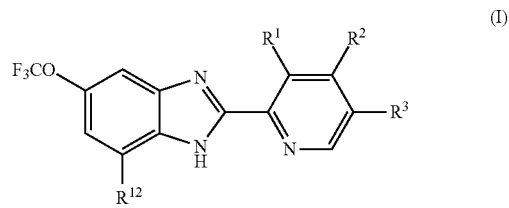

In the compounds of the invention, $R^1$, $R^2$ and $R^3$ are independently selected from H, $C_1$-$C_4$ alkoxy, $CO_2H$, $NR^4R^5$, and $OR^6$ where $R^6$ is a group of formula (II) or of formula (IIIa-f):

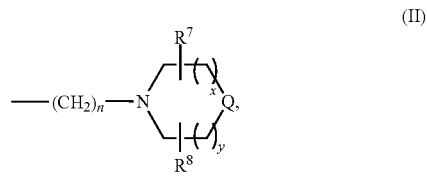

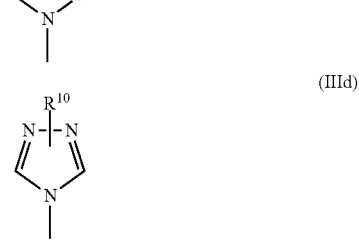

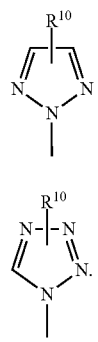 (IIIe)

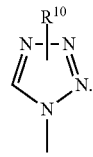 (IIIf)

The invention also includes pharmaceutically acceptable salts of the compounds of formula (I).

As mentioned above, $R^1$, $R^2$ and $R^3$ are independently selected from H, $C_1$-$C_4$ alkoxy, $CO_2H$, and $NR^4R^5$ but at least one of $R^1$, $R^2$ and $R^3$ is not H. In those embodiments, when one or more of $R^1$, $R^2$ and $R^3$ is a $C_1$-$C_4$ alkoxy it may be a methoxy group, an ethoxy group, a propoxy group, an iso-propoxy group, a butoxy group, an iso-butoxy group or a tert-butoxy group. In certain embodiments at least one of $R^1$, $R^2$ and $R^3$ is a methoxy group. When one or more of $R^1$, $R^2$ and $R^3$ are $NR^4R^5$, $R^4$ and $R^5$ are each independently H or $C_1$-$C_3$ alkyl or together with the nitrogen carrying them form a pyrrolidine or a piperidine ring. When one of $R^4$ and $R^5$ is a $C_1$-$C_3$ alkyl, it may be a methyl group, an ethyl group, a propyl group or an iso-propyl group. In certain embodiments, $R^4$ and $R^5$ are both a methyl group.

$R^1$, $R^2$ and $R^3$ may also be $OR^6$ where $R^6$ is a group of formula (II) or of formula (IIIa-f):

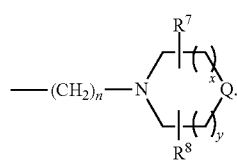 (II)

When $R^6$ is a group of formula (II), n ranges from 1-3. The value of n may in one embodiment be 1, in another 2 or in another 3. $R^7$ and $R^8$ are each independently H, methyl or ethyl. In certain embodiments $R^7$ and $R^8$ are both H. $R^7$ and $R^8$ may also be methyl. In one embodiment $R^7$ and $R^8$ are bound to a carbon atom adjacent the group Q or, when Q is a bond, to the carbon atoms joined by that bond.

In formula (II), the group Q is O, N—$R^9$, or a bond; x is 0, 1 or 2; and y is 0, 1 or 2. When the group Q is O or N—$R^9$, the sum of x+y≥1. When Q is a bond, the sum x+y≥2. In one embodiment, Q is O or N—$R^9$ and both x and y are 1. When Q is a bond, in one embodiment x and y may both 1 or in another embodiment, x may be 2 and y may be 1 or vice versa.

In those embodiments where the group Q is N—$R^9$, $R^9$ is $C_1$-$C_3$ alkyl, benzyl, —C(O)phenyl, or a $(CH_2)_nR^{11}$ where $R^{11}$ is a group of formula (IVa-f):

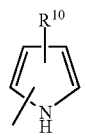 (IVa)

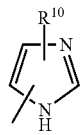 (IVb)

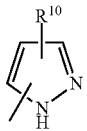 (IVc)

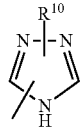 (IVd)

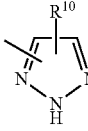 (IVe)

 (IVf)

When $R^9$ is $C_1$-$C_3$ alkyl, it may be a methyl group, an ethyl group, a propyl group or an iso-propyl group. In one particular embodiment $R^9$ is a benzyl group. When $R^9$ is a group of formula (IVa-f), the group $R^{10}$ is H, methyl, ethyl, phenyl or $CO_2H$. In one embodiment, $R^9$ is a group of formula (IVd) and $R^{10}$ is methyl or phenyl and may, for example, have the structure where the group is bound through a ring carbon:

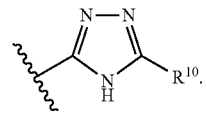

Alternatively a group of formula (IVa-f) may be bound through a ring nitrogen.

In another embodiment $R^1$, $R^2$ and $R^3$ may also be $OR^6$ where $R^6$ is a group of formula (IIIa-f):

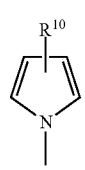 (IIIa)

(IIIb)
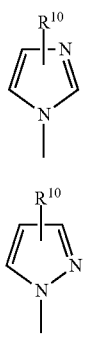

(IIIc)

(IIId)
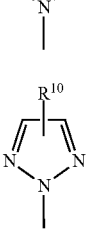

(IIIe)
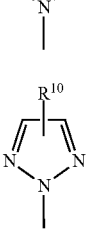

(IIIf)
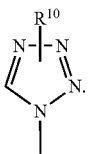

When $R^6$ is a group of formula (IIIa-f) it is bound to the nitrogen atom when Q is N—$R^6$ as indicated. A group of formula (IIIa-f) has a group $R^{10}R^{10}$ is H, methyl, ethyl, phenyl or $CO_2H$. In one embodiment, $R^{10}$ is a group of formula (IIIe) and $R^{10}$ is methyl or phenyl and may, for example, have a structure:

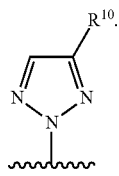

In the compounds of formula (I), the substituent RU is H or $(CH_2)_n$—$CO_2H$. In one embodiment $R^{12}$ is H.
In another embodiment, $R^{12}$ is $(CH_2)_n$—$CO_2H$ where n ranges from 1-3. The value of n may in one embodiment be 1, in another 2 or in another 3.

Exemplary compounds within formula (I), which individually represent separate embodiments of the invention are:

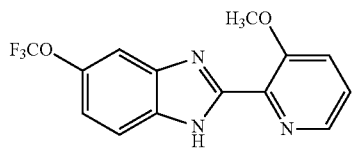 [SMILES: COc1cccnc1-c1nc2cc(OC(F)(F)F)ccc2[nH]1] 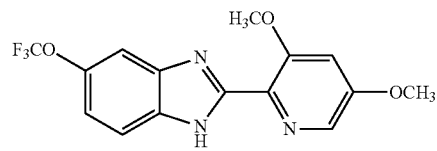

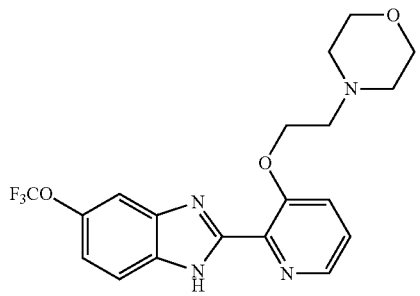 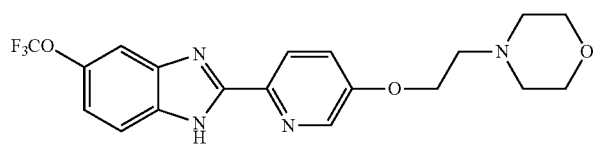

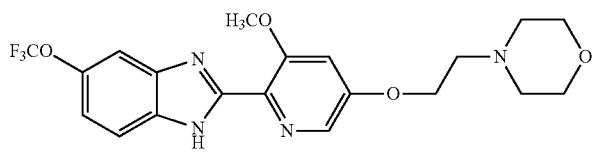

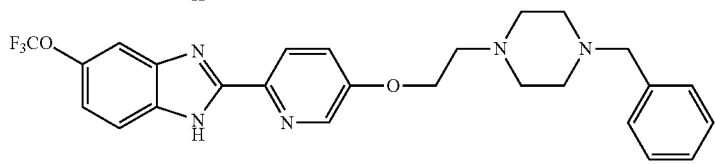

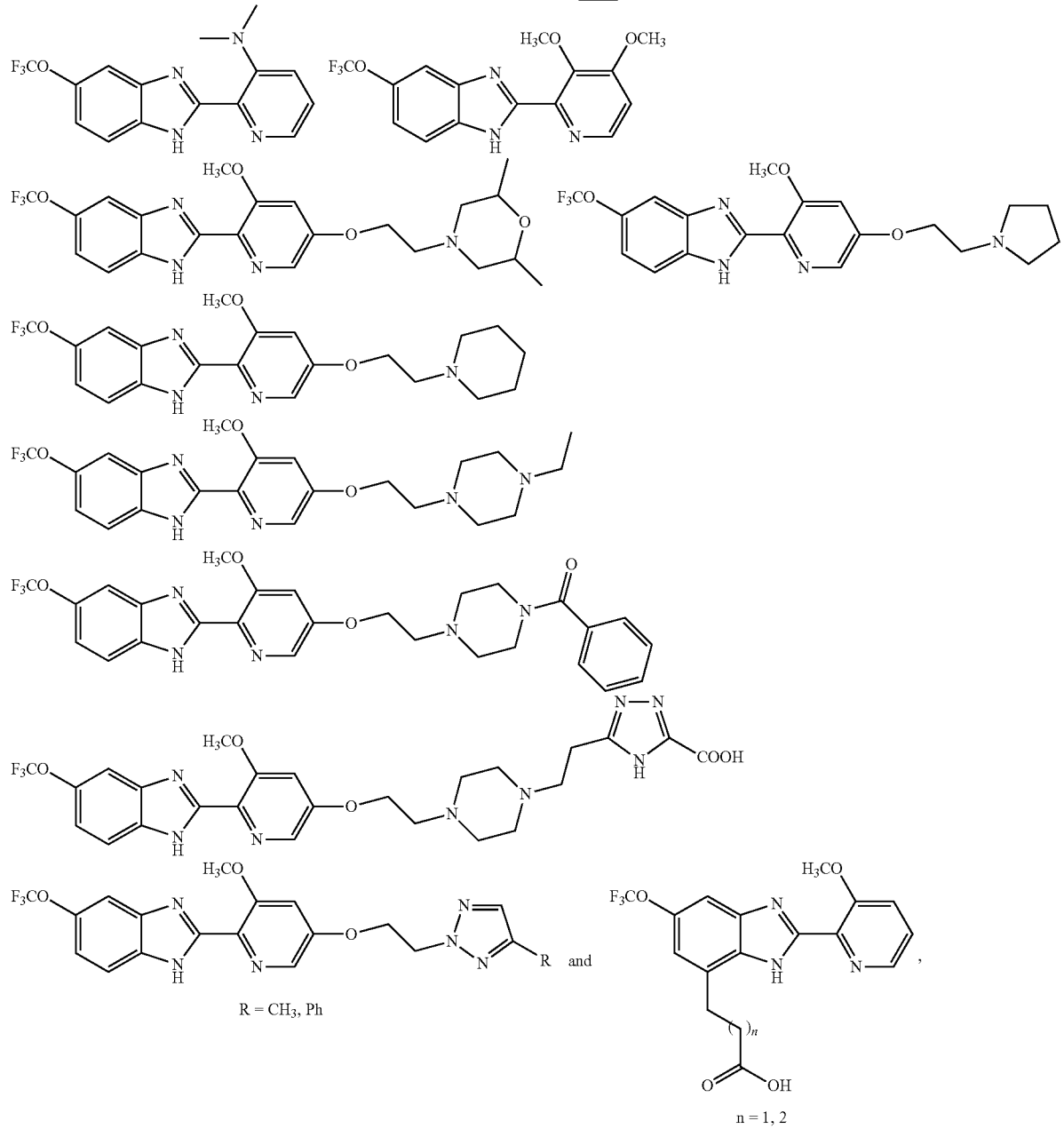

and pharmaceutically acceptable salts thereof.

As discussed above, the compounds of the invention are compounds of formula (I) and their pharmaceutically acceptable salts. The term "pharmaceutically acceptable salt" refers to salts that retain the biological effectiveness and properties of the compounds of the invention and that are not biologically or otherwise undesirable. In many cases, the compounds of the invention are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include, but are not limited to, hydrochloric acid, hydrobromic acid, sulfuric acid, nitric acid, phosphoric acid, and the like. Salts derived from organic acids include, but are not limited to, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Pharmaceutical Compositions Containing the Compounds of the Invention

The invention also relates to pharmaceutical compositions comprising a compound described herein and a pharmaceutically acceptable carrier (also known as a pharmaceutically acceptable excipient).

A pharmaceutical composition of the invention may be in any pharmaceutical form which contains a compound of the invention. The pharmaceutical composition may be, for example, a tablet, a capsule, a liquid suspension, an injectable composition, a topical composition, an inhalable composition or a transdermal composition. Liquid pharmaceutical compositions may be prepared comprising a compound of the invention. The pharmaceutical compositions generally contain, for example, about 0.1% to about 99.9% by weight of a compound of the invention, for example, about 0.5% to about 99% by weight of a compound of the invention and, for example, 99.5% to 0.5% by weight of at least one suitable pharmaceutical excipient. In one embodiment, the composition may be between about 5% and about 75% by weight of a compound of the invention with the rest being at least one suitable pharmaceutical excipient or at least one other adjuvant, as discussed below.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used.

For a liquid pharmaceutical composition of a compound of the invention or its salt (e.g., hydrochloride HCl salt), solubilizing agents that improve drug aqueous solubility, such as, for example, cyclodextrins, can be used. One non-limiting example of a cyclodextrin is a polyanionic variably substituted sulfobutyl ether of β-cyclodextrin (β-CD) (Captisol®).

For a solid pharmaceutical composition of the invention, the carrier in a solid pharmaceutical composition should not substantially alter the compound. Nor should the carrier be otherwise incompatible with the compound used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, a compound of the invention may be admixed with at least one pharmaceutically acceptable excipient such as, for example, sodium citrate or dicalcium phosphate or (a) (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing a compound of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Compositions of the invention may be intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the Invention from about 0.1 to about 90% w/v (weight per unit volume).

In addition to the topical method of administration described above, there are various methods of administering the compounds of the invention topically to the lung. One such means could involve a dry powder inhaler formulation of respirable particles comprised of the compounds of the invention, which the patient being treated inhales. It is common for a dry powder formulation to include carrier particles, to which the compound particles can adhere to. The carrier particles may be of any acceptable pharmacologically inert material or combination of materials. For example, the carrier particles may be composed of one or more materials selected from sugar alcohols; polyols, for example sorbitol, mannitol or xylitol, and crystalline sugars, including monosaccharides and disaccharides; inorganic salts such as sodium chloride and calcium carbonate; organic salts such as sodium lactate; and other organic compounds such as urea, polysaccharides, for example cyclodextrins and dextrins. The carrier particles may be a crystalline sugar, for example, a monosaccharide such as glucose or arabinose, or a disaccharide such as maltose, saccharose, dextrose or lactose, The compound of the invention would be dispersed into the respiratory tract, and subsequently contact the lower lung in a pharmaceutically effective amount.

In addition to the topical method of administration described above, there are various methods of administering the compounds of the invention systemically by such methods. One such means would involve an aerosol suspension of respirable particles comprised of the compounds of the invention, which the patient being treated inhales. The compound would be absorbed into the bloodstream via the lungs in a pharmaceutically effective amount. The respirable particles can be liquid or solid, with a particle size sufficiently small to pass through the mouth and larynx upon inhalation.

Dosage forms for oral administration, which includes capsules, tablets, pills, powders, granules, and suspensions may be used. Dosage forms for pulmonary administration, which includes metered dose inhaler, dry powder inhaler or aerosol formulations may be used. In such solid dosage forms, the active compound may be mixed with at least one inert, pharmaceutically acceptable excipient (also known as a pharmaceutically acceptable carrier).

A compound according to the invention may also be used to formulate liquid or injectable pharmaceutical compositions. Administration of a compound of the invention in pure form or in an appropriate pharmaceutical composition may be carried out via any of the accepted modes of administration or agents for serving similar utilities. Thus, administration may be, for example, orally, buccally, nasally, pulmonary, parenterally (intravenous, intramuscular, intraperitoneal, or subcutaneous), topically, transdermally, intravaginally, intravesically, intrasystemically, ophthalmically or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

Generally, the concentration of the compound(s) of the invention in a liquid composition, such as a lotion or injectable solution, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

Therapeutic Uses of the Compounds of the Invention

The invention further relates to the therapeutic use for the compounds disclosed herein. Compounds of the invention are effective in treating RUNX-signaling-dependent cancers that expresses wild-type CBFβ.

As used herein, "cancer" or "malignancy" refers to any of a number of diseases that are characterized by uncontrolled, abnormal proliferation of cells, the ability of affected cells to spread locally or through the bloodstream and lymphatic system to other parts of the body (i.e., metastasize), as well as any of a number of characteristic structural and/or molecular features. A "cancerous" or "malignant cell" is understood as a cell having specific structural properties, lacking differentiation and being capable of invasion and metastasis. Examples of cancers include, but are not limited to, blood (leukemia), breast, lung, ovarian, brain, bone, liver, kidney, colon, and prostate cancer. (See DeVita, V. et al. (eds.), 2001, Cancer Principles and Practice of Oncology, 6th. Ed., Lippincott Williams & Wilkins, Philadelphia, Pa.; this reference is herein incorporated by reference in its entirety for all purposes).

In one embodiment, the invention relates to methods of treating a RUNX-signaling-dependent cancer that expresses wild-type CBFβ in a subject in need thereof comprising administering to the subject a therapeutically effective amount of a compound of the invention. In another embodiment, the invention relates to methods of treating a cancer selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and/or adenocarcinoma, where the methods involve comprising administering to the subject a therapeutically effective amount of a compound of the invention. In another embodiment, the compounds of the invention can be used to treat a RUNX-signaling-dependent leukemia that expresses wild-type CBFβ, lung cancer, ovarian cancer, and/or breast cancer.

A separate embodiment of the invention involves methods of treating a RUNX-signaling-dependent cancer that expresses wild-type CBFβ in a subject in need thereof comprising administering to the subject a pharmaceutical composition of the invention. In a further embodiment of such methods, the cancer is selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and/or adenocarcinoma. In another embodiment, the pharmaceutical compositions of the invention can be used to treat a RUNX-signaling-dependent leukemia that expresses wild-type CBFβ, lung cancer, ovarian cancer, and/or breast cancer.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary.

The actual amount required for treatment of any particular disease, disorder or condition for any particular patient may depend upon a variety of factors including, for example, the particular disease, disorder or condition being treated; the disease state being treated and its severity; the specific pharmaceutical composition employed; the age, body weight, general health, sex and diet of the patient; the mode of administration; the time of administration; the route of administration; and the rate of excretion of a compound of the invention; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

The amount of a compound of the invention, or a salt thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 200 mg/kg or from about 0.5 to about 100 mg/kg, e.g., from about 10 to about 75 mg/kg of body weight per day, such as 3 to about 50 mg/kg body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple injections or by direct or topical application.

EXAMPLES

Chemical Synthesis:

Commercially obtained reagents were used as received. All reagents and anhydrous solvents used for Grignard reaction were freshly distilled. Progress of reactions was monitored by TLC performed on Analtech 250 micron silica gel GF plates visualized with 254 nm UV light and also by mass spectrometry using a Waters single-quadrupole LCMS. All compounds were purified on Biotage Isolera Four Flash Chromatography system, using SNAP cartridges. Melting points were determined on a Mel-Temp manual melting point apparatus with a Fluke 51II thermocouple. $^1$H and $^{13}$C NMR spectra were recorded on a Bruker NMR spectrometer at 600 and 800 MHz in CDCl$_3$, DMSO-d$_6$, and MeOH-d$_4$ with TMS as internal standard. Chemical shift values are reported in δ ppm units. Mass spectra were recorded on a Micromass AutoSpec Ultima Magnetic sector mass spectrometer in positive ESI mode.

Fluorescence Resonance Energy Transfer (FRET) Assay:

As described in U.S. Pat. No. 8,748,618 and published PCT application WO2010/132684, a FRET assay can be used to effectively monitor the inhibition of CBF binding to the Runt domain of RUNX proteins (as well as for CBFβ-SMMHC binding to the Runt domain of RUNX proteins).

For the assay, the green fluorescent protein derivative Cerulean is fused to the N-terminus of the Runt domain and the green fluorescent protein derivative Venus to the N-terminus of CBFβ (Gorczynski, M. J., J. Grembecka, et al. (2007), "Allosteric inhibition of the protein-protein interaction between the leukemia-associated proteins Runx1 and CBF-beta." Chem Biol 14(10): 1186-97), or to CBFβ-SMMHC (Illendula, A. et al. Chemical biology. A small-molecule inhibitor of the aberrant transcription factor CBFbeta-SMMHC delays leukemia in mice. Science 347, 779-784, doi:10.1126/science.aaa0314 (2015)). The ratio of the emission intensities at 525 nm and 474 nm, measured after excitation at 433 nm, was used as the readout in this assay. The dynamic range for the FRET assay was determined by adding a 30-fold excess of untagged CBFβ (or CBFβ-SMMHC) to the assay and the associated change in the FRET ratio was defined as 100% inhibition. The CBFβ-RUNX1 Runt domain assay was validated by determining the $K_d$ for binding using serial dilution resulting in a $K_d$ value of 70 nM, in good agreement with the $K_d$ value of 57 nM obtained from calorimetric measurements of the binding of unmodified RUNX1 Runt domain to unmodified CBFβ (Lukasik, S. M., L. Zhang, et al. (2002), "Altered affinity of CBFbeta-SMMHC for Runx1 explains its role in leukemogenesis." Nat Struct Biol 9(9): 674-9).

Example 1—Comparative Compounds

The following compounds 2a-2c, 3a-f, 4a-4i, 5a-l, 6a-c, and 7a-d were prepared by a reductive cyclization method as described by Illendula, A. et al. Chemical biology. A small-molecule inhibitor of the aberrant transcription factor CBF-beta-SMMHC delays leukemia in mice. Science 347, 779-784, doi:10.1126/science.aaa0314 (2015). All synthesized compounds were purified by flash chromatography and characterized by NMR and mass prior to evaluation in a FRET assay. Table 1 shows the chemical structures of the compounds for which $IC_{50}$ was determined in a FRET assay measuring inhibition of CBFβ binding to the RUNX1 Runt domain, as described above. "NA" Indicates "not active."

5-methoxy-2-phenyl-1H-benzo[d]imidazole (2a), CAS Registry Number 79877-53-5;
2-(furan-2-yl)-5-methoxy-1H-benzo[d]imidazole (2b), CAS Registry Number 517901-94-9;
2-(5-methoxy-1H-benzo[d]imidazol-2-yl)phenol (2c), CAS Registry Number 939752-51-9;
2-(pyridin-2-yl)-1H-benzo[d]imidazole (3a), CAS Registry Number 1137-68-4;
5-ethoxy-2-(pyridin-2-yl)-1H-benzo[d]imidazole (3b), CAS Registry Number 84123-79-5;
5-fluoro-2-(pyridin-2-yl)-1H-benzo[d]imidazole (3c), CAS Registry Number 875468-81-8;
5-methyl-2-(pyridin-2-yl)-1H-benzo[d]imidazole (3d), CAS Registry Number 7471-12-7;
5-phenyl-2-(pyridin-2-yl)-1H-benzo[d]imidazole (3e), CAS Registry Number 14060-65-2;
2-(pyridin-2-yl)-5-(trifluoromethyl)-1H-benzo[d]imidazole (3f), CAS Registry Number 1256094-37-7;
4-methoxy-2-(pyridin-2-yl)-1H-benzo[d]imidazole (4a), CAS Registry Number 68118-46-7;
4-ethoxy-2-(pyridin-2-yl)-1H-benzo[d]imidazole (4b), CAS Registry Number 1256094-25-3;
4-methyl-2-(pyridin-2-yl)-1H-benzo[d]imidazole (4c), CAS Registry Number 68118-45-6;
2-(pyridin-2-yl)-4-(trifluoromethyl)-1H-benzo[d]imidazole (4d), CAS Registry Number 1256094-38-8;
4,5-dimethyl-2-(pyridin-2-yl)-1H-benzo[d]imidazole (4e) CAS Registry Number 89481-12-9;
5,6-difluoro-2-(pyridin-2-yl)-1H-benzo[d]imidazole (4f), CAS Registry Number 1256094-32-2;
5-methoxy-2-(6-methoxypyridin-2-yl)-1H-benzo[d]imidazole (4g), CAS Registry Number 1256094-58-2;
5-methoxy-2-(6-methylpyridin-2-yl)-1H-benzo[d]imidazole (4h); CAS Registry Number 67273-50-1;
2-(6-fluoropyridin-2-yl)-5-methoxy-1H-benzo[d]imidazole (4i); CAS Registry Number 1256094-60-6;
5-isopropoxy-2-(pyridin-2-yl)-1H-benzo[d]imidazole (5a), CAS Registry Number 1256094-26-4;
2-(pyridin-2-yl)-5-(trifluoromethoxy)-1H-benzo[d]imidazole (5b), CAS Registry Number 1256094-31-1;
5-(methylthio)-2-(pyridin-2-yl)-1H-benzo[d]imidazole (5c), CAS Registry Number 1256094-29-7;
2-(pyridin-2-yl)-1H-benzo[d]imidazole-5-carboxylic acid (5d), CAS Registry Number 669070-64-8;
2-(pyridin-2-yl)-1H-benzo[d]imidazole-5-carboxamide (5e), CAS Registry Number 1256094-43-5;
N,N-dimethyl-2-(pyridin-2-yl)-1H-benzo[d]imidazol-5-amine (5f), CAS Registry Number 889664-39-5;
2-(pyridin-2-yl)-5-(pyrrolidin-1-yl)-1H-benzo[d]imidazole (5g), CAS Registry Number 1256094-40-2;
5-(piperidin-1-yl)-2-(pyridin-2-yl)-1H-benzo[d]imidazole (5h), CAS Registry Number 1256094-41-3;
4-(2-(pyridin-2-yl)-1H-benzo[d]imidazol-5-yl)morpholine (5I), CAS Registry Number 1256094-42-4;
4,6-dichloro-2-(pyridin-2-yl)-1H-benzo[d]imidazole (5j), CAS Registry Number 1256094-36-6;
5-chloro-6-methoxy-2-(pyridin-2-yl)-1H-benzo[d]imidazole (5k), CAS Registry Number 1256094-35-5;
4,5,6-trifluoro-2-(pyridin-2-yl)-1H-benzo[d]imidazole (5l), CAS Registry Number 1256094-33-3;
5-methoxy-2-(5-methoxypyridin-2-yl)-1H-benzo[d]imidazole (6a), CAS Registry Number 1256094-47-9;
5-methoxy-2-(5-(2-methoxyethoxy)pyridin-2-yl)-1H-benzo[d]imidazole (6b), CAS Registry Number 1256094-49-1;
5-methoxy-2-(4-methoxypyridin-2-yl)-1H-benzo[d]imidazole (6c), CAS Registry Number 1256094-56-0;
5-methoxy-2-(3-methoxypyridin-2-yl)-1H-benzo[d]imidazole (7a), CAS Registry Number 1256094-51-5;
2-(3-methylpyridin-2-yl)-5-(trifluoromethoxy)-1H-benzo[d]imidazole (7b), CAS Registry Number 1256094-53-7;
5-(trifluoromethoxy)-2-(3-(trifluoromethyl)pyridin-2-yl)-1H-benzo[d]imidazole (7c), CAS Registry Number 1256094-55-9; and
2-(3-fluoropyridin-2-yl)-5-(trifluoromethoxy)-1H-benzo[d]imidazole (7d), CAS Registry Number 1256094-54-8.

Structure-Activity Relationships (SAR)

The above compounds 2a-2c, 3a-f, 4a-4i, 5a-l, 6a-c, and 7a-d were used to assess possible substitutions to compound AI-4-57 (shown below). AI-4-57 inhibits the binding of CBF-SMMHC to the RUNX1 Runt domain having a 50% inhibitory concentration ($IC_{50}$) of 22 μM. U.S. Pat. No. 8,748,618. Using the FRET assay, we showed that this compound is, as expected, also a modest potency inhibitor of the binding of wild-type CBFβ to the RUNX1 Runt domain with $IC_{50}$ of 34 μM (see Table 1).

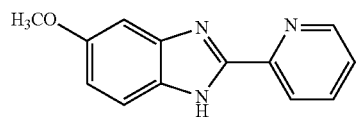

AI-4-57

As shown in Schemes 1-3 several regions of Al-4-57 were evaluated to define a pharmacophore for activity.

Scheme 1. Replacement of pyridine moiety

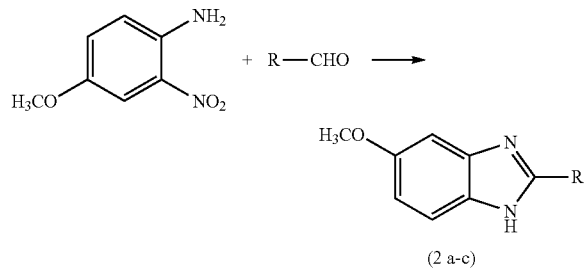

(2 a-c)

a) R = Ph
b) R = 2-furyl
c) R = 2-OH-Phenyl

Scheme 2. Replacement of —OCH3

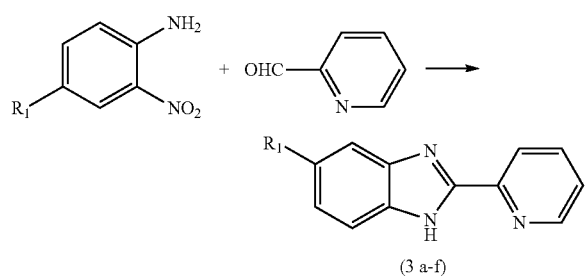

(3 a-f)

a) R₁ = H
b) R₁ = OC₂H₅
c) R₁ = F
d) R₁ = Me
e) R₁ = Ph
f) R₁ = Benzyl
g) R₁ = CF₃

Scheme 3. Substitutions on the benzimidazole and pyridine moiety

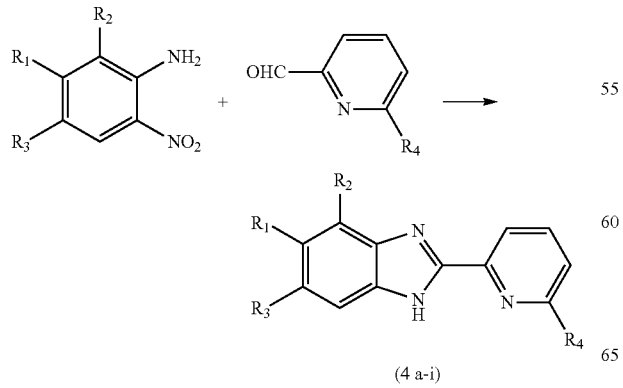

(4 a-i)

-continued a) $R_2$ = OCH₃
b) $R_2$ = OC₂H₅
c) $R_2$ = CH₃
d) $R_2$ = CF₃
e) $R_1$ = $R_2$ = CH₃
f) $R_1$ = $R_3$ = F
g) $R_1$ = $R_4$ = OCH₃
h) $R_1$ = OCH₃; $R_4$ = CH₃
i) $R_1$ = OCH₃; $R_4$ = F Substitution of the pyridine ring with a phenyl ring (2a) or a furan (2b) resulted in a complete loss of activity. Replacement of the methoxy functionality with a hydrogen (3a) also resulted in a complete loss of activity. FIG. 1 shows the results of STD NMR analysis of Al-4-57 binding to CBFβ (Mayer, M. & Meyer, B. Characterization of ligand binding by saturation transfer difference NMR spectroscopy. *Angewandte Chemie-International Edition* 38, 1784-1788 (1999); Mayer, M. & Meyer, B. Group epitope mapping by saturation transfer difference NMR to identify segments of a ligand in direct contact with a protein receptor. *J Am Chem Soc* 123, 6108-6117 (2001)). When short saturation times are used for this experiment, it can be effectively used to map epitopes on a molecule which are in close contact with the protein. With a short saturation time of 500 ms, the signal for the methyl group of the methoxy functional group as well as the signal for the neighboring 4 hydrogen of the benzimidazole ring are observed in the difference spectrum, consistent with this portion of the molecule being in close contact with the protein as well as with the effect of removing this substituent on activity.

The structure-activity relationship at the 5-position of Al-5-47 was examined by introducing fluorine (3c), triflouromethyl (3g), methyl (3d), and ethoxy (3b) substitutions. Introduction of trifluoromethyl or methyl resulted in a loss of activity whereas introduction of fluorine or ethoxy resulted in compounds with similar activity to Al-4-57. Moving the 5-methoxy to the 4-position (4a) resulted in reduced activity. Methyl and methoxy substitutions ortho to the pyridine nitrogen (position 6 in pyridine ring (4g, 4h) resulted in inactive compounds. As shown in FIG. 1, short saturation time STD NMR identifies the hydrogen ortho to the pyridine nitrogen as being in close contact with the protein, providing a rationale for the loss of activity observed with substitutions at this position.

TABLE 1

| Compound | Structure | FRET IC$_{50}$ (µM) |
|---|---|---|
| Al-4-57 | H₃CO-benzimidazole-pyridine | 34.3 ± 0.3 |
| 2a | H₃CO-benzimidazole-phenyl | NA |

TABLE 1-continued

| Compound | Structure | FRET IC$_{50}$ (μM) |
|---|---|---|
| 2b | H₃CO-benzimidazole-furan | NA |
| 3b | EtO-benzimidazole-pyridine | ≥ 34.3 ± 0.3 |
| 3c | F-benzimidazole-pyridine | ≥ 34.3 ± 0.3 |
| 3d | H₃C-benzimidazole-pyridine | NA |
| 3f | F₃C-benzimidazole-pyridine | NA |
| 4a | OCH₃-benzimidazole-pyridine | ≥ 34.3 ± 0.3 |
| 4g | H₃CO-benzimidazole-pyridine-OCH₃ | NA |
| 4h | H₃CO-benzimidazole-pyridine-CH₃ | NA |
| 4i | H₃CO-benzimidazole-pyridine-F | NA |

Example 2

Example 2.1: Synthesis of 3,5-Disubstituted Pyridine-2-Aldehydes and Benzimidazole Starting Materials The following substituted pyridine-2-aldehydes, were prepared accordingly in multi-step synthesis by using appropriate intermediates as described previously.

3-methoxypicolinaldehyde, CAS Registry Number 1849-53-2;

3,5-dimethoxypicolinaldehyde, CAS Registry Number 1256790-69-8;

3methyl 2-formylnicotinate, CAS Registry Number 25230-59-5;

2-formylnicotinic acid, CAS Registry Number 23590-67-2;

2-formylnicotinamide, CAS Registry Number 951924-56-4;

3-(dimethylamino) picolinaldehyde, CAS Registry Number 1780942-71-3;

3,4-dimethoxypicolinaldehyde, CAS Registry Number 142470-53-9;

3-(pyrrolidin-1-yl) picolinaldehyde, CAS Registry Number 1707358-09-5; and 5-hydroxy-3-methoxypicolinaldehyde, CAS Registry Number 1289039-21-9.

These pyridine-2-aldehydes were used in the preparation of compounds as described below and shown in Scheme 1.

Example 2.2: General Procedure for the Synthesis of Substituted Benzimidazoles (Scheme 4)

To a solution of appropriately substituted aldehyde (1.0 mmol) and 2-nitro-5-(trifluoromethoxy)aniline (1.0 mmol) in ethanol (4 mL) and DMSO (0.2 mL, 5%), a sodium dithionite solution (0.52 g, 3 mmol in 3 mL water) was added. The reaction mixture was refluxed for 8 hours or followed by TLC until the completion of the reaction. The solvent was removed under reduced pressure, diluted with water, and neutralized with aqueous NH₄OH solution. After usual work up the crude reaction mixtures were purified by flash chromatography by using appropriate solvent systems and evaporation of the solvents led to viscous compounds or solids. The slowly solidifying precipitate/viscous compounds were dissolved in a minimal amount of dichloromethane and triturated with hexanes, stirring overnight at r.t to get a clear solid compounds. The solid thus obtained was filtered, and dried under vacuum to give substituted benzimidazoles. The physical characterization of each compound synthesized is reported in Table 2.

Scheme 4

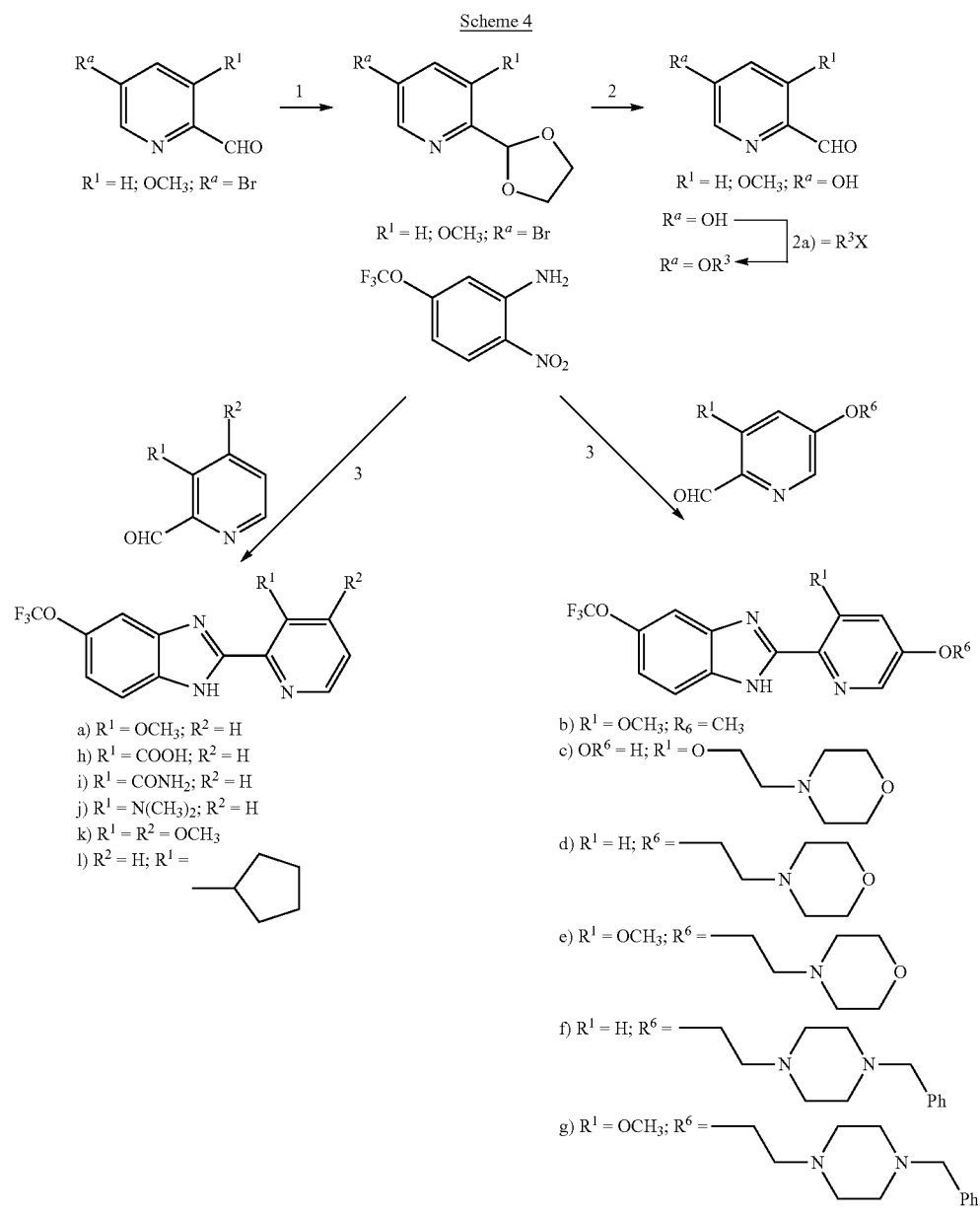

1. Ethane-1, 2-diol, TsOH, toluene, reflux, 8 h
2. Pd$_2$(dba)$_3$, Tetramethyl tBuXPhos, KOH, dioxane/water, reflux, 16 h
2a. R$^6$—Cl, K$_2$CO$_3$, DMF, 70° C., 8 h
3. Aldehyde, Na$_2$S$_2$O$_4$, EtOH/water, 80° C., 8 h

TABLE 2

| Name | Structure | MP (° C.) | $^1$H-NMR | $^{13}$C-NMR | HRMS |
|---|---|---|---|---|---|
| Al-10-104 | (F$_3$CO-benzimidazole-MeO-pyridine structure) | 165-167 | $^1$H-NMR (800 MHz, MeOD): δ 4.10 (3H, s), 7.22-7.23 (1H, d, J = 8.00 Hz), 7.51-7.53 (1H, dd, J = 8.00, 8.00 Hz), 7.61 (1H, s), 7.69-7.71 (1H, d, J = 8.00 Hz), 7.74-7.75 (1H, d, J = | $^{13}$C-NMR (800 MHz, MeOD): δ 56.48, 118.04, 121.49, 121.70, 122.96, 124.23, 127.44, 137.47, | m/z [M + H]$^+$ calcd for C$_{14}$H$_{10}$F$_3$N$_3$O$_2$ 310.0798; found: 310.0797 |

TABLE 2-continued

| Name | Structure | MP (° C.) | ¹H-NMR | ¹³C-NMR | HRMS |
|---|---|---|---|---|---|
| | | | 8.00 Hz), 7.74-7.75 (1H, d, J = 8.00 Hz), 8.37-8.38 (1H, d, J = 8.00 Hz) | 142.74, 146.63, 152.66, 156.44 | |
| Al-12-16 | 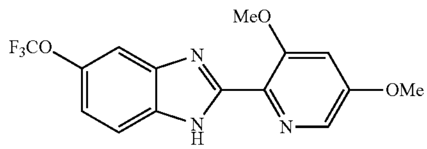 [SMILES: COc1cnc(-c2nc3cc(OC(F)(F)F)ccc3[nH]2)c(OC)c1] | 164-166 | ¹H-NMR (600 MHz, MeOD): δ 3.98 (3H, s), 4.08 (3H, s), 7.15-7.17 (1H, d, J = 8.6 Hz), 7.20 (1H, s), 7.54 (1H, s), 7.65-7.67 (1H, d, J = 8.5 Hz), 8.07 (1H, s) | | m/z [M + H]⁺ calcd for $C_{15}H_{12}F_3N_3O_3$ 340.0904; found: 340.0905 |
| Al-14-55 | 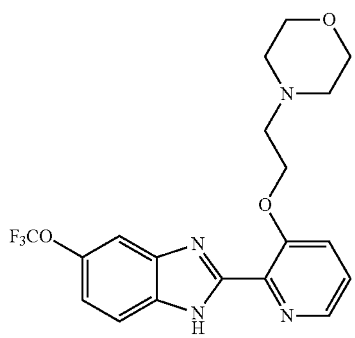 [SMILES: FC(F)(F)Oc1ccc2[nH]c(-c3ncccc3OCCN3CCOCC3)nc2c1] | >250 | ¹H-NMR (800 MHz, MeOD): δ 2.63 (4H, s), 2.96-2.97 (2H, t), 3.68-3.69 (4H, t), 4.46-4.47 (2H, t), 7.26-7.28 (1H, d, J = 8.4 Hz), 7.54-7.56 (1H, dd, J = 8.40, 8.40 Hz), 7.63 (1H, s), 7.66-7.77 (2H, d, J = 8.00 Hz), 8.41-8.42 (1H, d, J = 8.00 Hz) | ¹³C-NMR (800 MHz, MeOD): δ 54.99, 58.29, 67.54, 67.87, 117.30, 118.21, 120.43, 121.70, 122.96, 123.27, 124.23, 127.49, 138.32, 143.47, 146.67, 152.58, 155.63 | m/z [M + H]⁺ calcd for $C_{19}H_{19}F_3N_4O_3$ 409.1482; found: 409.1485 |
| Al-12-126 | 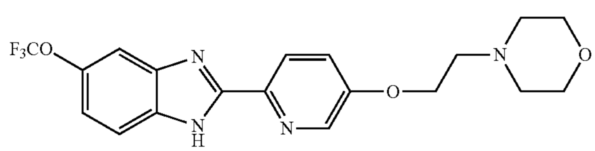 [SMILES: FC(F)(F)Oc1ccc2[nH]c(-c3ccc(OCCN4CCOCC4)cn3)nc2c1] | 135-137 | ¹H-NMR (800 MHz, MeOD): δ 2.63 (4H, s), 2.86-2.87 (2H, t), 3.74-3.75 (4H, t), 4.29-4.30 (2H, t), 7.20-7.21 (1H, d, J = 5.36 Hz), 7.50-7.73 (3H, m), 8.23-8.24 (1H, d, J = 8.40 Hz), 8.44 (1H, d, J = 2.72 Hz) | ¹³C-NMR (800 MHz, MeOD): δ 55.24, 58.65, 67.28, 67.79, 106.02, 112.27, 113.63, 117.49, 118.36, 120.55, 121.67, 122.74, 122.94, 123.80, 134.63, 135.85, 139.62, 141.55, 143.56, 145.04, 146.28, 154.73, 157.86 | m/z [M + H]⁺ calcd for $C_{19}H_{19}F_3N_4O_3$ 409.1482; found: 409.1482 |
| Al-14-91 | 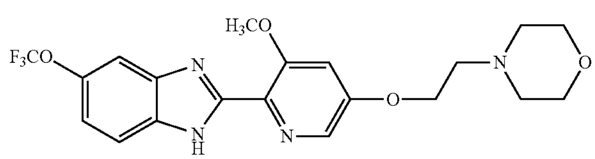 [SMILES: COc1cc(OCCN2CCOCC2)cnc1-c1nc2cc(OC(F)(F)F)ccc2[nH]1] | 94-96 | ¹H-NMR (800 MHz, MeOD): δ 2.62 (4H, s), 2.84-2.86 (2H, t), 3.71-3.73 (4H, m), 4.07 (3H, s), 4.30-4.32 (2H, t), 7.17-7.18 (1H, d, J = 8.4 Hz), 7.20-7.21 (1H, d, J = 2.24 Hz), 7.55 (1H, s), 7.67-7.68 (1H, d, J = 8.4 Hz), 8.08-8.09 (1H, | ¹³C-NMR (800 MHz, MeOD): δ 55.24, 56.61, 58.69, 67.49, 67.78, 106.99, 109.42, 116.87, 117.71, 120.44, | m/z [M + H]⁺ calcd for $C_{20}H_{21}F_3N_4O_4$ 439.1588; found: 439.1593 |

| Name | Structure | MP (° C.) | ¹H-NMR | ¹³C-NMR | HRMS |
|---|---|---|---|---|---|
| | | | d, J = 1.4 Hz) | 121.70, 122.96, 124.23, 130.15, 131.00, 146.41, 152.93, 157.52, 159.07 | |
| Al-14-95 | 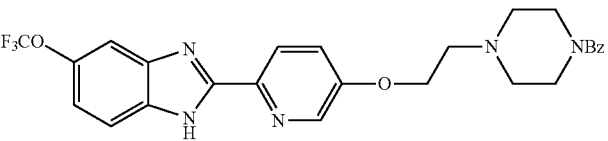 Bz = benzyl | 111-114 | ¹H-NMR (800 MHz, MeOD): δ 2.59 (4H, s), 2.70 (4H, s), 2.90-2.91 (2H, t), 3.58 (2H, s), 4.31-4.32 (2H, t), 7.21-7.22 (1H, d, J = 7.2 Hz), 7.28-7.29 (1H, m), 7.33-7.36 (4H, m), 7.50-7.74 (3H, m), 8.25-8.26 (1H, d, J = 8.64 Hz), 8.45-8.46 (1H, d, J = 2.72 Hz) | | m/z [M + H]⁺ calcd for $C_{26}H_{26}F_3N_5O_2$ 498.2111; found: 498.2113 |
| Al-14-100 | 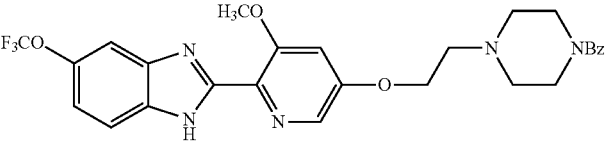 Bz = benzyl | 192-194 | ¹H-NMR (800 MHz, MeOD): δ 2.59 (4H, s), 2.70 (4H, s), 2.90-2.91 (2H, t), 3.58 (2H, s), 4.10 (3H, s), 4.34-4.35 (2H, t), 7.19-7.20 (1H, dd, J = 1.5, 8.16 Hz), 7.24-7.25 (1H, d, J = 2.24 Hz), 7.28-7.29 (1H, m), 7.33-7.36 (4H, m), 7.58 (1H, s), 7.69-7.70 (1H, d, J = 8.3 Hz), 8.11-8.12 (1H, d, J = 2.08 Hz) | ¹³C-NMR (800 MHz, MeOD): δ 53..74, 54.37, 56.64, 58.15, 64.00, 67.68, 107.10, 117.67, 121.71, 122.97, 128.65, 129.49, 130.27, 130.89, 131.03, 138.29, 146.43, 152.97, 157.53, 159.08 | m/z [M + H]⁺ calcd for $C_{27}H_{28}F_3N_5O_3$ 528.2217; found: 528.2219 |
| Al-12-150 | 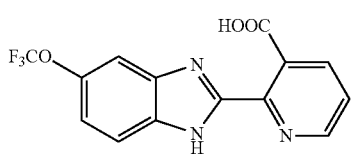 | 235-238 | ¹H-NMR (800 MHz, MeOD): δ 7.33-7.34 (1H, dd, J = 1.4, 8.72 Hz), 7.66 (1H, s), 7.68-7.70 (1H, dd, J = 8.00, 8.00 Hz), 7.78-7.79 (1H, d, J = 8.00 Hz), 8.65-8.66 (1H, dd, J = 1.44, 8.00 Hz), 8.89-8.90 (1H, dd, J = 1.1, 5.4 Hz) | ¹³C-NMR (800 MHz, MeOD): δ 109.53, 117.62, 119.55, 120.32, 121.59, 122.86, 124.13, 126.62, 130.47, 136.54, 138.16, 142.56, 145.82, 147.43, 152.94, 153.34 169.01 | m/z [M + H]⁺ calcd for $C_{14}H_8F_3N_3O_3$ 324.0591; found: 324.0592 |

TABLE 2-continued

| Name | Structure | MP (° C.) | ¹H-NMR | ¹³C-NMR | HRMS |
|---|---|---|---|---|---|
| Al-12-149 | 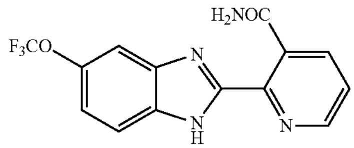 [SMILES: NC(=O)c1cccnc1-c1nc2cc(OC(F)(F)F)ccc2[nH]1] | >250 | ¹H-NMR (800 MHz, MeOD): δ 7.22 (1H, s), 7.57-7.69 (3H, m), 8.06-8.07 (1H, m), 8.80-8.81 (1H, d, J = 8.00 Hz) | ¹³C-NMR (800 MHz, MeOD): δ 104.25, 111.93, 115.75, 116.98, 118.87, 120.14, 121.40, 122.66, 124.04, 132.27, 136.76, 144.80, 149.91, 151.85, 173.04 | m/z [M + H]⁺ calcd for $C_{14}H_9F_3N_4O_2$ 323.0750; found: 323.0753 |
| Al-14-18 | 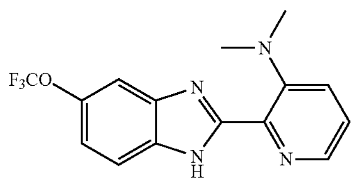 [SMILES: CN(C)c1cccnc1-c1nc2cc(OC(F)(F)F)ccc2[nH]1] | 189-191 | ¹H-NMR (800 MHz, MeOD): δ 2.77 (6H, s), 7.24-7.25 (1H, dd, J = 1.5, 8.60 Hz), 7.44-7.46 (1H, dd, J = 8.32, 8.32 Hz), 7.61 (1H, s), 7.69-7.70 (1H, dd, J = 1.2, 8.30 Hz), 7.73-7.74 (1H, d, J = 8.70 Hz), 8.30-8.31 (1H, dd, J = 1.3, 4.4 Hz) | ¹³C-NMR (600 MHz, MeOD): δ 43.97, 109.37, 118.04, 120.43, 121.70, 122.96, 124.23, 126.65, 127.78, 140.72, 142.93, 146.58, 150.90, 154.37 | m/z [M + H]⁺ calcd for $C_{15}H_{13}F_3N_4O$ 323.1114; found: 323.1116 |
| Al-14-72 | 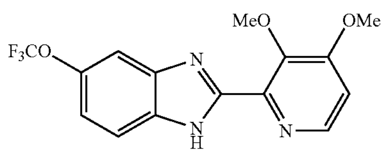 [SMILES: COc1ccnc(-c2nc3cc(OC(F)(F)F)ccc3[nH]2)c1OC] | 96-99 | ¹H-NMR (800 MHz, MeOD): 3.97 (3H, s), 4.04 (3H, s), 7.22-7.24 (2H, m), 7.62 (1H, s), 7.74-7.75 (1H, d, J = 8.00 Hz), 8.39-8.34 (1H, d, J = 5.4 Hz) | ¹³C-NMR (800 MHz, MeOD): δ 56.91, 61.85, 110.55, 118.13, 120.43, 121.70, 122.96, 124.23, 141.91, 146.66, 146.88, 147.72, 152.41, 161.72 | m/z [M + H]⁺ calcd for $C_{15}H_{12}F_3N_3O_3$ 340.0904; found: 340.0904 |
| Al-14-7 | 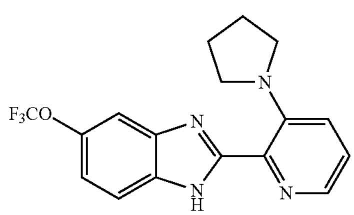 [SMILES: FC(F)(F)Oc1ccc2[nH]c(-c3ncccc3N3CCCC3)nc2c1] | 206-208 | ¹H-NMR (800 MHz, MeOD): δ 1.87-1.88 (4H, m), 3.06-3.08 (4H, m), 7.20-7.21 (1H, d, J = 8.4 Hz), 7.35-7.37 (1H, dd, J = 8.64, 8.64 Hz), 7.40-7.39 (1H, dd, J = 1.28, 8.64 Hz), 7.53 (1H, s), 7.66-7.65 (1H, d, 7.36 Hz), 8.06-8.07 (1H, dd, J = 1.2, 5.52 Hz) | ¹³C-NMR (800 MHz, MeOD): δ 26.81, 51.61, 105.98, 113.13, 113.30, 118.04, 118.45, 120.43, 121.46, 121.69, 121.86, 122.96, 123.60, 124.22, 126.42, 127.85, 127.91, 134.90, 138.57, | m/z [M + H]⁺ calcd for $C_{17}H_{15}F_3N_4O$ 349.1271; found: 349.1274 |

TABLE 2-continued

| Name | Structure | MP (° C.) | ¹H-NMR | ¹³C-NMR | HRMS |
|------|-----------|-----------|--------|---------|------|
| | | | | 138.93, 141.09, 146.46 146.73, 149.97, 155.47 | |

Example 2.3: FRET Assay of the Compounds in Table 2

Table 3 shows the $IC_{50}$ values for the compounds in Table 2, as well as compounds Al-4-57 and Al-10-47, determined using a FRET assay as described above. "NA" indicates not active. Previous work on the development of small molecule inhibitors that are specific for CBFβ-SMMHC showed that Al-4-57 has a short half-life in mice with loss of the methyl group on the methoxy functionality being the resulting metabolite (Illendula, A. et al. Chemical biology. A small-molecule inhibitor of the aberrant transcription factor CBF-beta-SMMHC delays leukemia in mice. *Science* 347, 779-784, doi:10.1126/science.aaa0314 (2015)). However, administration of Al-10-104 to mice via intraperitoneal (IP) injection resulted in significant sedative effects that were lethal at high doses. Reasoning that this effect depended on the ability of the compound to cross the blood brain barrier (BBB), compounds Al-12-126 and Al-14-91 have appended morpholine ring substituents to the 5 position of the pyridine ring to increase the polarity of the compounds and thereby limit BBB penetration. These compounds retain similar activity in the FRET assay to the parent compounds (see Table 3). Importantly, these compounds, when formulated as the HCl salts with Captisol® and administered IP at 100 mg/kg did not induce the sedative effects seen with Al-10-104 and were well-tolerated by mice. Measurements of the pharmacokinetic properties of these compounds in mice show that at a dose of 100 mg/kg, we can achieve useful concentrations of the compounds with reasonable half-lives in vivo (Al-14-91, oral gavage, $t_{1/2}$=203 minutes).

TABLE 3

| Compound ID | Structure | FRET $IC_{50}$ (µM) |
|-------------|-----------|---------------------|
| Al-4-57 comparative | [H₃CO-benzimidazole-pyridine structure] | 34.3 ± 0.3 |
| Al-10-47 comparative | [F₃CO-benzimidazole-pyridine structure] | 3.19 ± 0.5 |
| Al-10-104 | [F₃CO-benzimidazole-(H₃CO)pyridine structure] | 2.65 ± 0.18 |
| Al-12-16 | [F₃CO-benzimidazole-(H₃CO)(OCH₃)pyridine structure] | 1.69 ± 0.18 |
| Al-14-55 | [F₃CO-benzimidazole-pyridine with morpholinoethoxy substituent] | 4.83 ± 0.32 |

TABLE 3-continued

| Compound ID | Structure | FRET IC$_{50}$ (μM) |
|---|---|---|
| Al-12-126 | 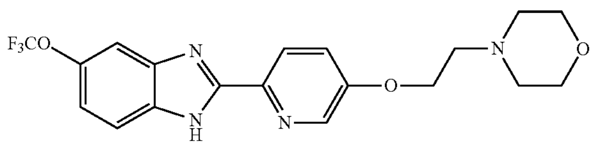 [SMILES: FC(F)(F)Oc1ccc2[nH]c(-c3ccc(OCCN4CCOCC4)cn3)nc2c1] | 8.91 ± 1.30 |
| Al-14-91 | 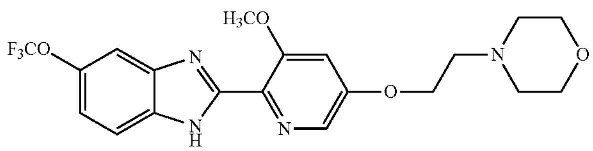 [SMILES: COc1cc(OCCN2CCOCC2)cnc1-c1nc2cc(OC(F)(F)F)ccc2[nH]1] | 2.97 ± 0.53 |
| Al-14-95 | 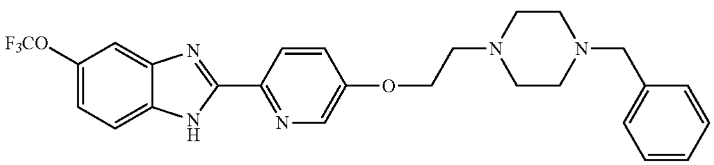 [SMILES: FC(F)(F)Oc1ccc2[nH]c(-c3ccc(OCCN4CCN(Cc5ccccc5)CC4)cn3)nc2c1] | 2.65 ± 0.19 |
| Al-14-100 | 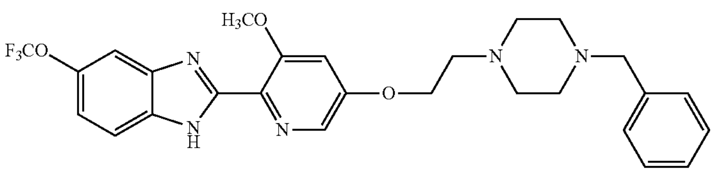 [SMILES: COc1cc(OCCN2CCN(Cc3ccccc3)CC2)cnc1-c1nc2cc(OC(F)(F)F)ccc2[nH]1] | 2.16 ± 0.03 |
| Al-12-150 | 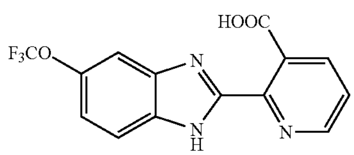 [SMILES: O=C(O)c1cccnc1-c1nc2cc(OC(F)(F)F)ccc2[nH]1] | 48.9 ± 1.6 |
| Al-12-149 | 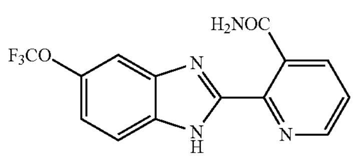 [SMILES: NC(=O)c1cccnc1-c1nc2cc(OC(F)(F)F)ccc2[nH]1] | NA |
| Al-14-18 | 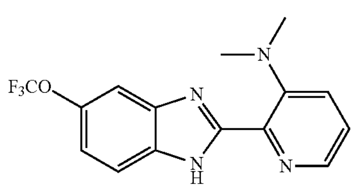 [SMILES: CN(C)c1cccnc1-c1nc2cc(OC(F)(F)F)ccc2[nH]1] | 4.97 ± 0.27 |
| Al-14-72 | 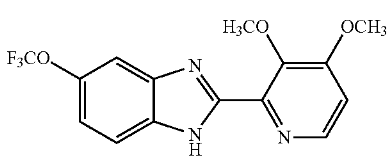 [SMILES: COc1ccnc(-c2nc3cc(OC(F)(F)F)ccc3[nH]2)c1OC] | 1.72 ± 0.23 |
| Al-12-139 | 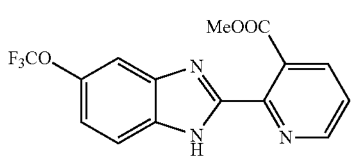 [SMILES: COC(=O)c1cccnc1-c1nc2cc(OC(F)(F)F)ccc2[nH]1] | NA |

Example 3—CBFβ Inhibitors Disrupt CBFβ-RUNX1 Binding in SEM Cells

To test whether the wild-type CBFβ Inhibitors can disrupt the binding of CBFβ to RUNX1 in cells, co-immunoprecipitation experiments were performed in the SEM cell line. Co-immunoprecipitation assays of lysates from acute myeloid leukemia SEM cells were treated with Al-4-88[1], Al-10-47, Al-10-104, Al-12-126 and Al-14-91 at 10 μM for 6 hours. RUNX1-bound CBFβ protein levels and immunoprecipitated RUNX1 are shown on the top panel of FIG. 2A. Quantification of RUNX1 bound CBFβ is shown on the bottom graph. Protein levels were normalized to RUNX1 and depicted relative to DMSO control.

[1] Al-4-88 is an inactive, control compound that has the following formula:

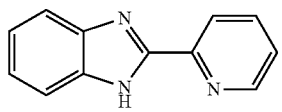 [SMILES: c1ccc(-c2nc3ccccc3[nH]2)nc1]

Figure 2A:
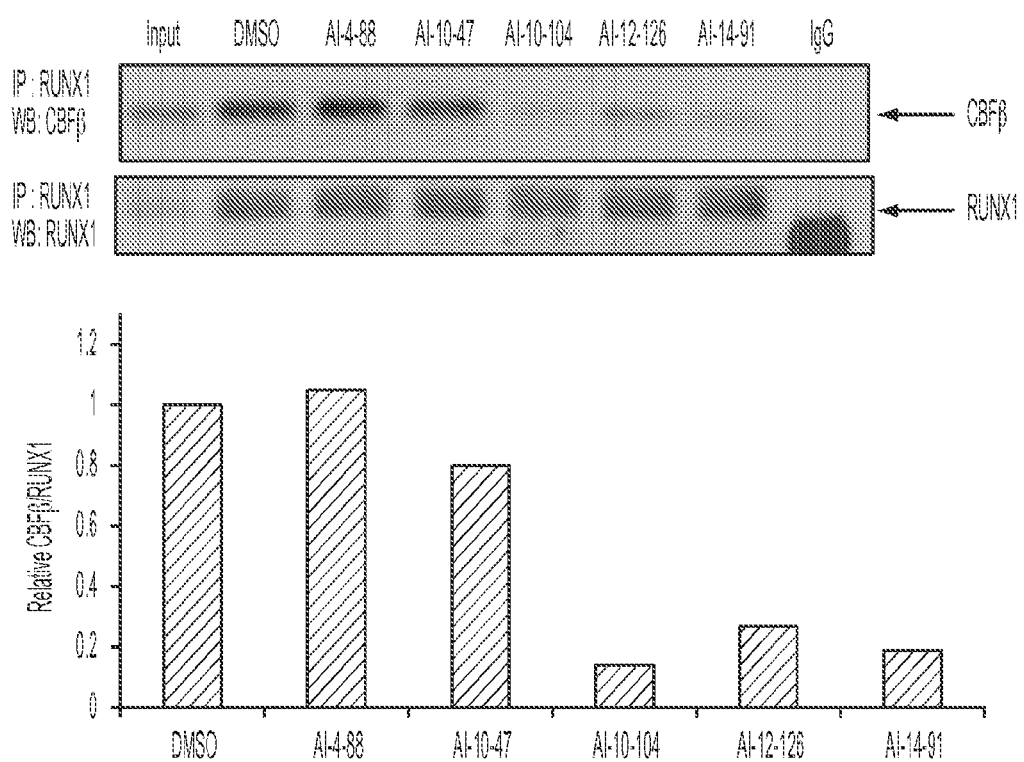
FIG. 2A. Binding of CBFβ to RUNX1 in cells treated with Al-4-88, Al-10-47, Al-10-104, Al-12-126, and Al-14-91.
Figures 2B, 3A:
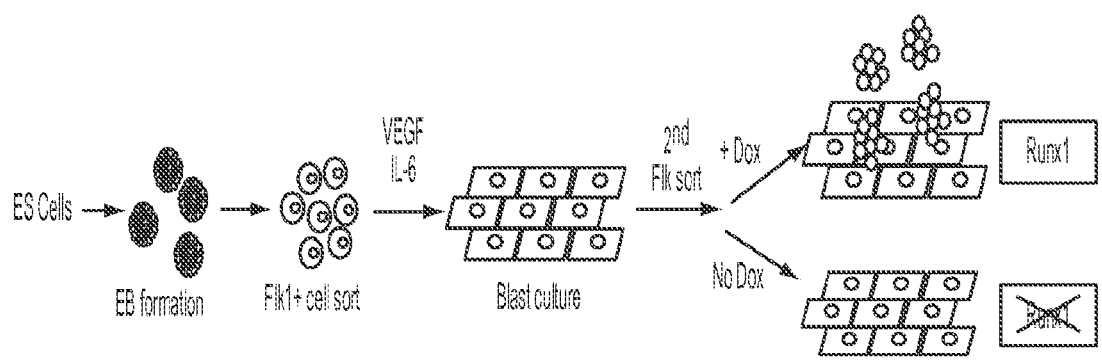
FIG. 2B. Aqueous solubility of compounds Al-4-88, Al-10-47, Al-10-104, Al-12-126, and Al-14-91.
FIG. 3A. Schematic diagram showing inducible Runx1 (iRx) ES cell differentiation system.

FIG. 2A demonstrates a reduction in binding of CBFβ binding to RUNX1 in cells treated with 10 μM Al-10-104, Al-12-126, and Al-14-91. As Al-10-47 showed only a modest effect, the aqueous solubility of all 5 compounds was tested in 0.25% DMSO by NMR spectroscopy, mimicking the conditions used for the coIP (FIG. 2B). Al-10-104, Al-12-126, and Al-14-91 were all soluble at concentrations above 100 μM. However, Al-10-47 was only soluble to 0.44 μM, explaining the reduced activity seen for Al-10-47 in this assay. As the Runt domain is highly conserved among all three RUNX family members, we would expect to see similar effects on binding to RUNX2 or RUNX3. Therefore, the action of the inhibitors will likely affect the activity of all three RUNX family members.

Example 4—Effects of CBFβ Inhibitors on RUNX1 Occupancy and Target Gene Expression FIG. 3A is a schematic diagram representing the inducible Runx1 (iRx) ES cell differentiation system. ES cells were allowed to form embryoid bodies (EB) in IVD culture media and hemangioblast Flk1 positive cells were sorted and seeded into blast culture media. After 2 days, a second Flk1 sort was performed and Flk1 positive cells were cultured in hemogenic endothelium culture conditions. In the absence of doxycycline (−dox), Runx1 is absent and cells cannot progress from the HE1 stage of development. In the presence of doxycycline (+dox), Runx1 is expressed and differentiation progresses, resulting in the formation of CD41+ve/c-kit+ve floating progenitors.

Figure 3B:
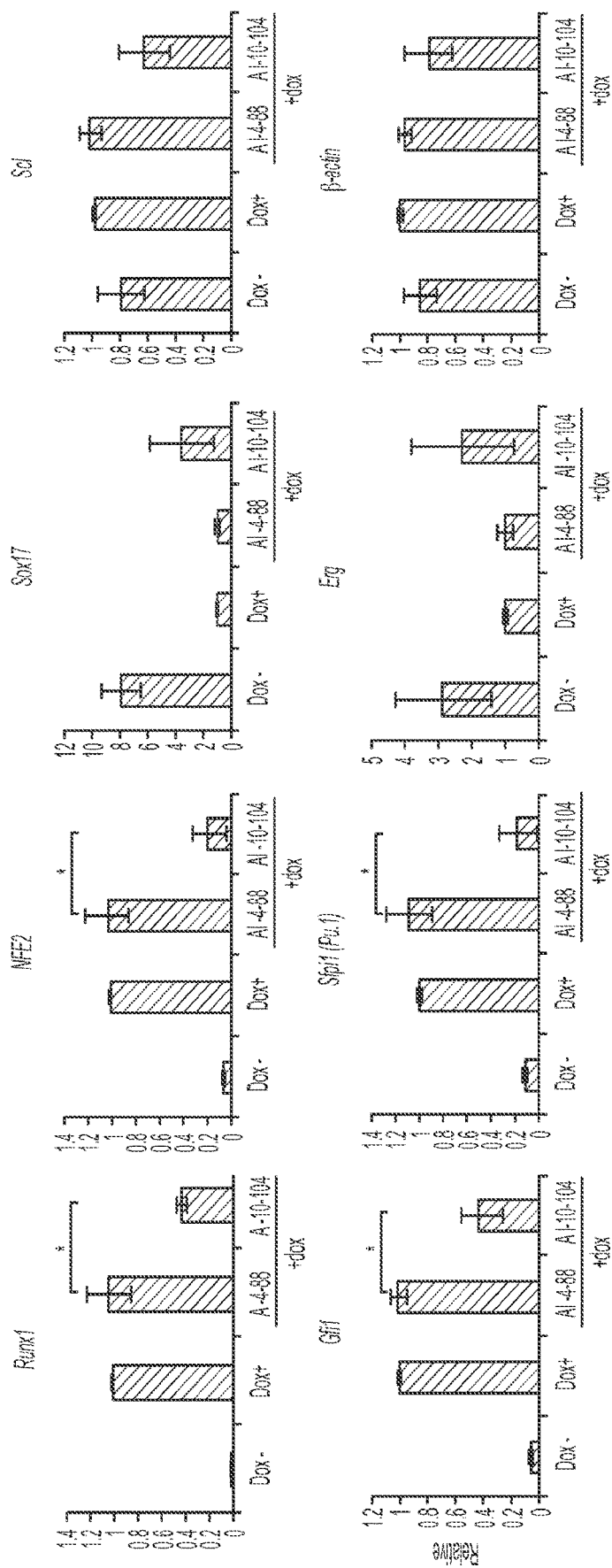
FIG. 3B. Gene expression of analysis (genes indicated) of cells treated with Al-4-88 and Al-10-104.

FIG. 3B shows gene expression analysis of inhibitor-treated cells using RNA prepared from cells treated with 10 μM Al-10-104 or 10 μM Al-4-88 in the presence of doxycycline. Relative expression of genes is shown, normalized to GAPDH and using +dox as the calibrator. Error bars represent standard deviation where n=3, with the exception of the −dox sample where n=2 and dots represent the minimum and maximum values. *=p<0.05 according to a t-test analysis comparing control and inhibitor compound.

FIG. 3C provides representative FACS histograms showing staining of the surface markers CD41 and c-kit in cells treated with the compounds and in the presence or absence of doxycycline, as indicated. The results demonstrated that the percentage of cells expressing c-kit and CD41 is reduced by treatment with 10 μM Al-10-104, but not with the control compound Al-4-88.

FIG. 3D provides representative FACS histograms showing staining of Annexin V and Propidium Iodide (PI) in cells treated with compounds Al-10-104 and Al-4-88 in the absence or presence of doxycycline, as indicated. Annexin V and PI staining is similar in each of the conditions indicating that apoptosis is not increased by Al-10-104 in the adherent cells harvested.

Figure 3E:
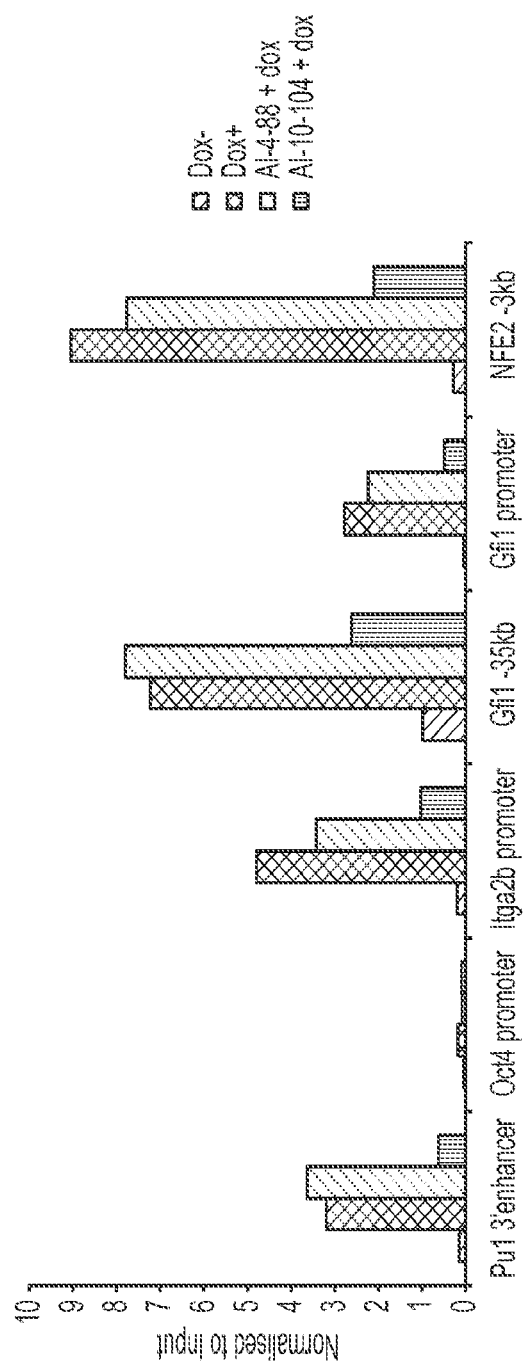
FIG. 3E. ChIP analysis of HA-Runx1 binding following Runx1 induction by doxycycline and treatment with Al-4-88 or Al-10-104.

FIG. 3E shows ChIP analysis of HA-Runx1 binding following Runx1 induction by doxycycline and treatment with inhibitor or control compound. ChIP with an anti-HA antibody recognizing HA tagged Runx1 was used to identify Runx1 binding at selected amplicons and enrichment normalized to input, one representative experiment is shown.

Figure 4:
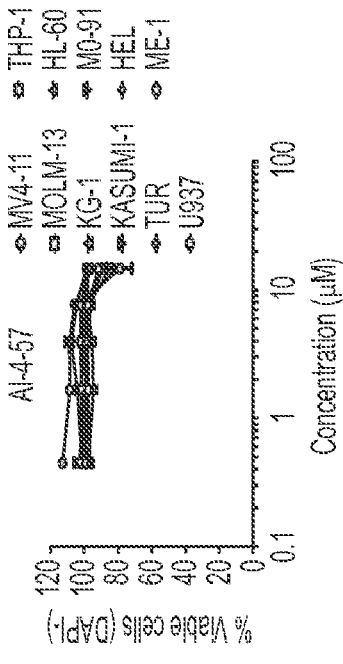
FIG. 4. Viability of for 11 leukemia cell lines treated with Al-4-88, Al-4-47, Al-4-57, Al-10-104, and Al-14-91.
Figure 4:
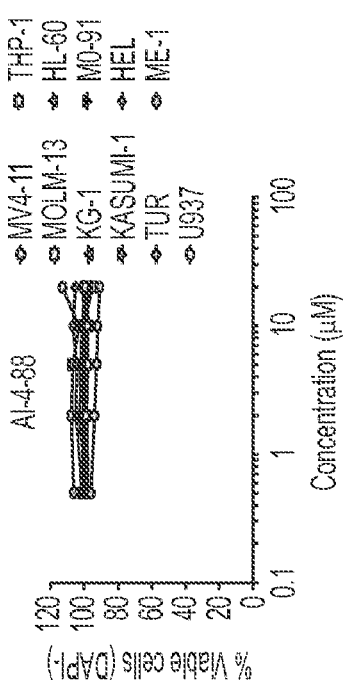
Figure 4:
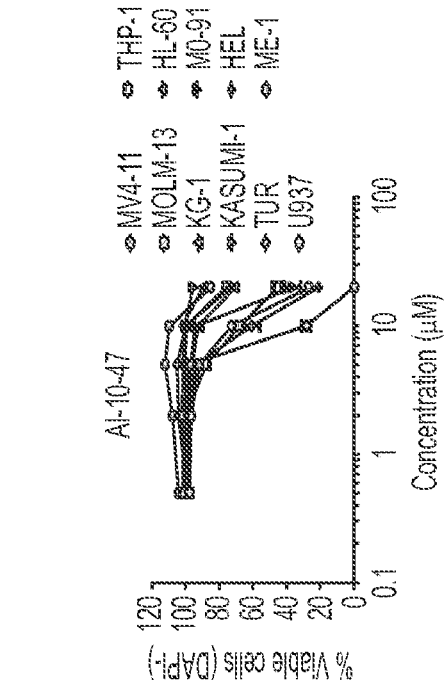
Figure 4:
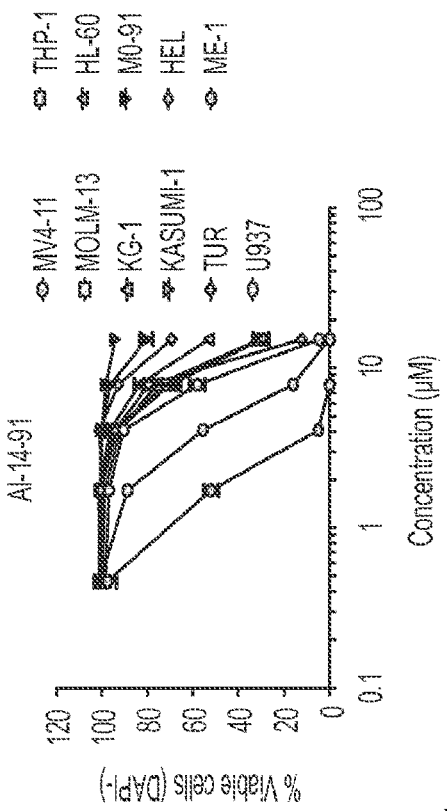
Figure 4:
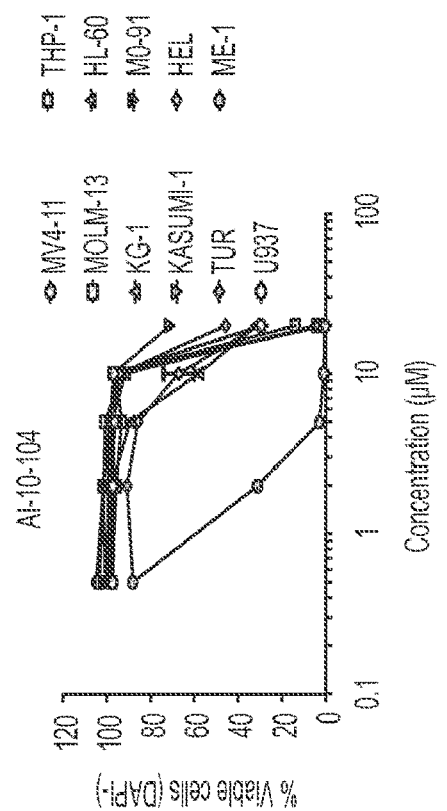

Example 5—Effects of CBFβ Inhibitors on the Viability of a Panel of Leukemia Cell Lines Compounds Al-4-88, Al-4-57, Al-10-47, Al-10-104, and Al-14-91 were screened against a panel of 11 leukemia cell lines with varying genotypes. FIG. 4 shows percent viability for 11 leukemia cell lines after 48 hours of treatment with the indicated compounds. No activity was observed for the inactive control compound Al-4-88, and the modest-potency Al-4-57 showed only very weak activity. However, for all the more active inhibitors tested (Al-10-47, Al-10-104, and Al-14-91), significant inhibition of the majority of the cell lines was observed.

The ME-1 cell line showed the greatest sensitivity. The viability is represented as the percent DAPI negative cells relative to DMSO control. Each symbol/color in the graphs of FIG. 4 represent an individual cell line. The symbol represents the mean of independent replicates and the error bars represent the SEM. The table indicates the morphology, type of leukemia, and known mutations for each of the 11 cell lines.

Figure 5:
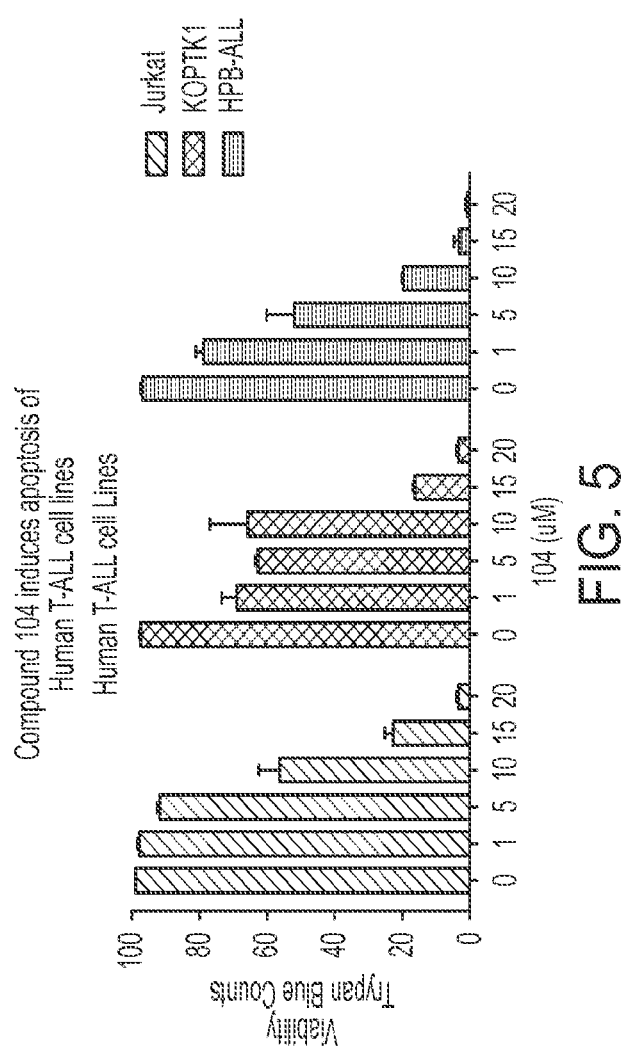
FIG. 5. Al-10-104 induces apoptosis in human T-ALL cell lines.
Figure 6:
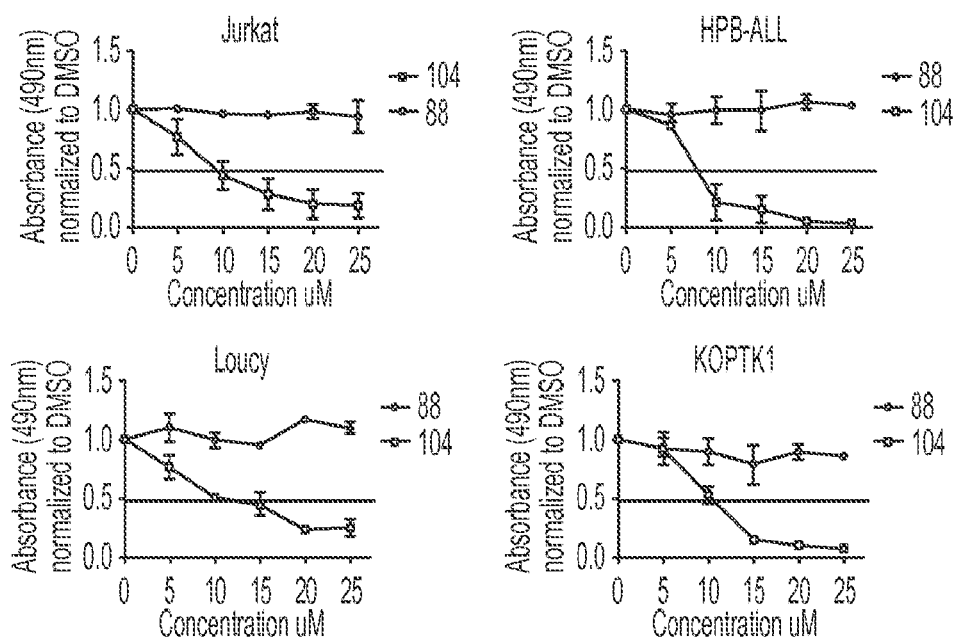
FIG. 6. Al-10-104 reduces proliferation of human T-ALL cell lines.

Example 6—Compound 104 Induces Apoptosis of Human Leukemia T-ALL Cell Lines and MLL-AF4 Lines FIG. 5 demonstrates that the monomer compound Al-10-104 induced apoptosis in T-ALL cell lines. This compound also inhibited proliferation of the following T-ALL cell lines: Jurkat, HBP-ALL, Loucy, and KOPTK1 (FIG. 6), but the inactive compound Al-4-88 did not have such an effect.

Figure 7:
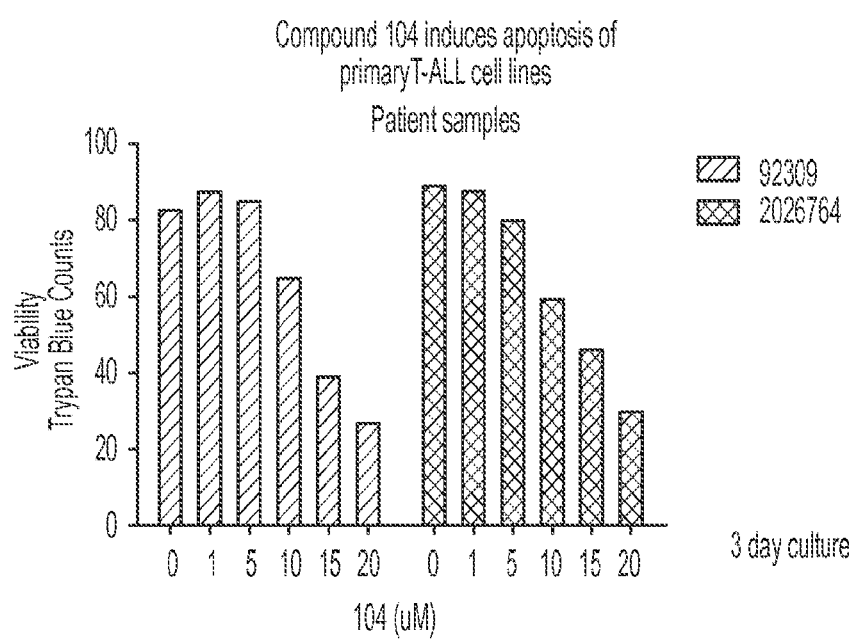
FIG. 7. Al-10-104 induced apoptosis of primary T-ALL patient samples.

FIG. 7 shows that Al-10-104 induced apoptosis of primary T-ALL patient samples. A dose-dependent response was demonstrated in two different patient samples. Al-10-104 induced apoptosis even in GSI resistant patient samples.

Figure 8:
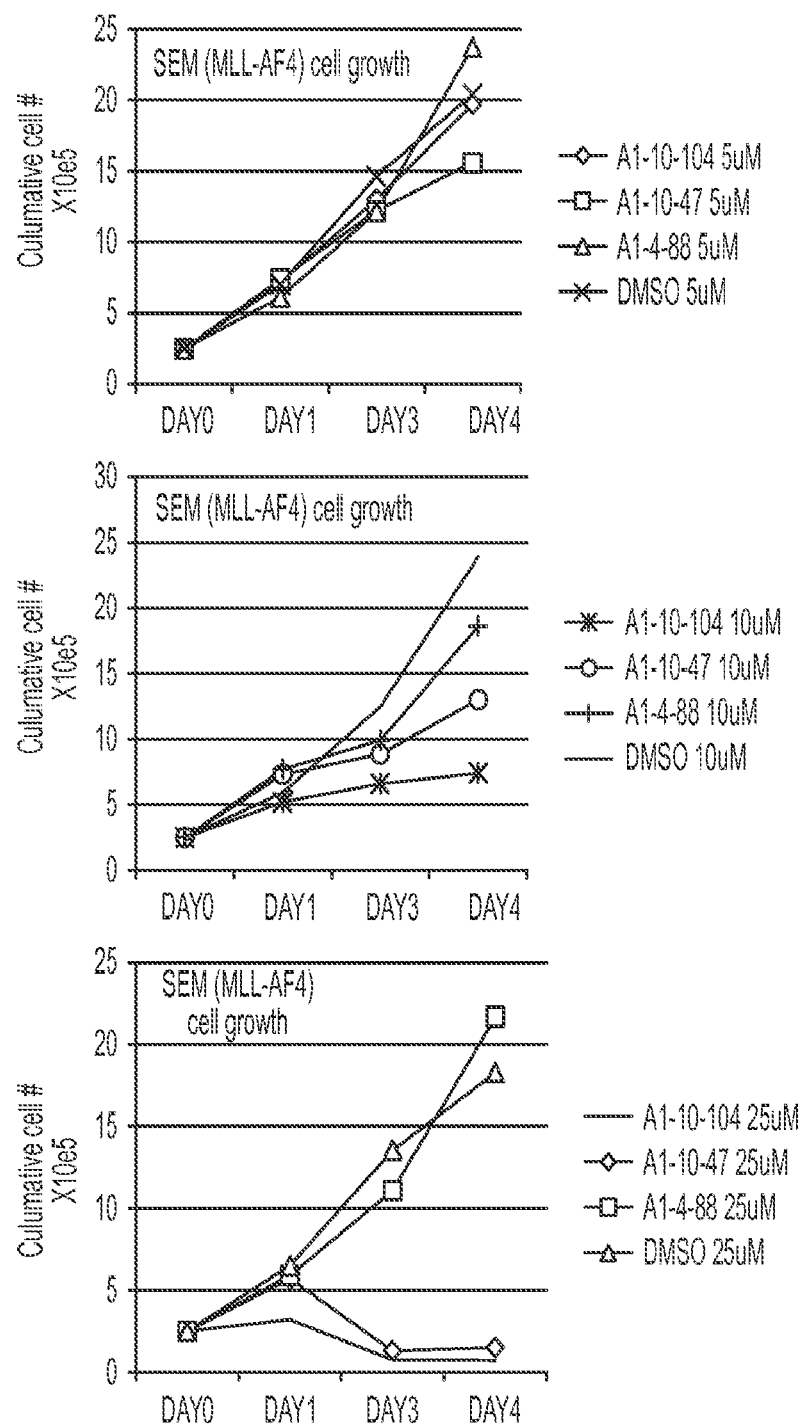
FIG. 8. Al-10-104 and Al-10-47 induce cell death of MLL-AF4 leukemia cell line.

FIG. 8 demonstrates that compounds Al-10-104 and Al-10-47, but not the inactive control compound Al-4-88, induced cell death of MLL-AF4 leukemia cells (three graphs).

Example 7—Effects of CBFβ Inhibitors on Adni Formation by MCF10A-5E Cells and Viability of Basal-Like Breast Cancer Cell Line HC1143

CBFβ inhibitors altered acinar morphogenesis of the basal-like (triple negative) breast epithelial cells and blocked survival of basal-like breast cancer cells in 3D organotypic culture. To evaluate whether CBFβ inhibition would influence the multicellular organization of basal-like breast epithelia, 3D culture of MCF10A-5E cells was used. Knockdown of RUNX1 in these cells delayed proliferation arrest and promoted the formation of nonspherical acini, indicating a role for RUNX1 during morphogenesis.

Figure 9A:
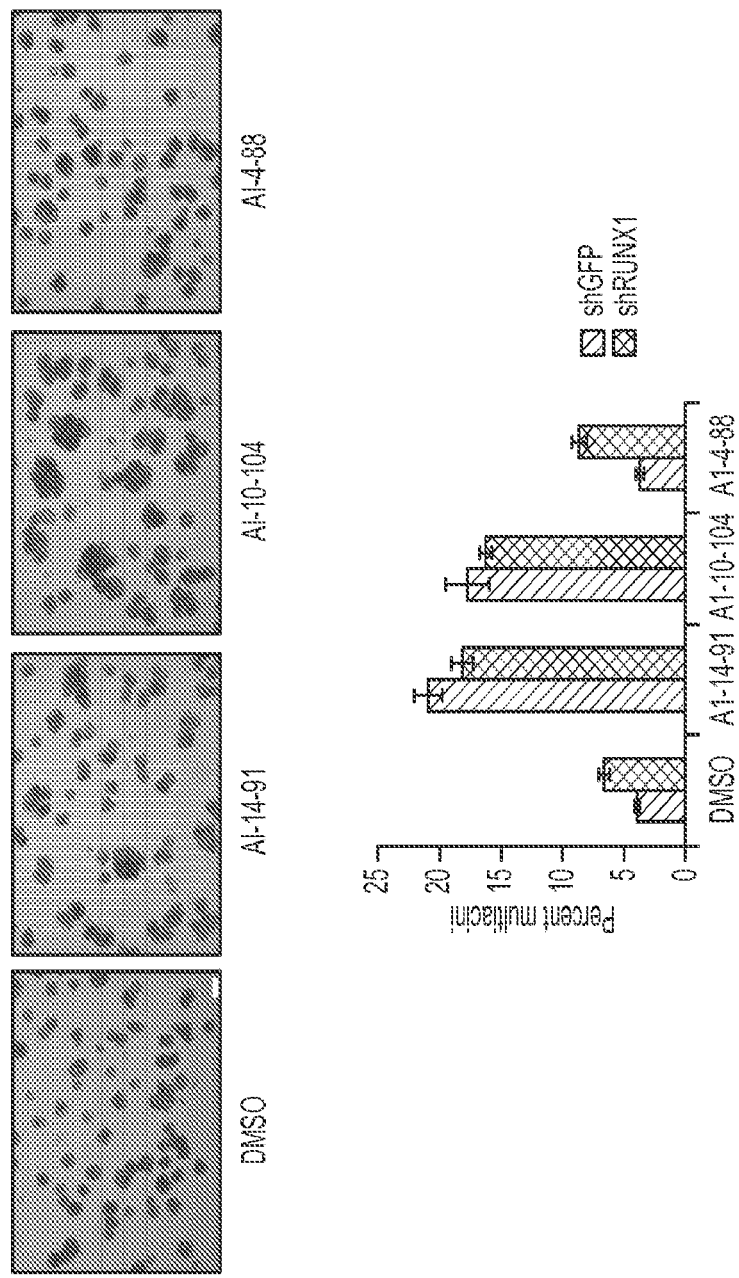
FIG. 9A. Brightfield microscopy images of 3D cultures of MCF10A-5E cells treated with Al-14-91, Al-10-104, and Al-4-88 and percent multiacini in MCF10A-5E cells stably expressing shRUNX1 or shGFP control.

When shRUNX1 or control cells were cultured with CBFβ inhibitors Al-10-104 and Al-14-91, it resulted in a dramatic increase in the formation of multiacinar structures compared to carrier control or inactive compound Al-4-88 (FIG. 9A). The extent of multiacinus formation greatly exceeded that of RUNX1 knockdown, suggesting a phenotypic role for other RUNX-family members such as RUNX2, which is also expressed in these cells. The multiacini resulting from CBFβ inhibition were not radially symmetric, thereby arguing against a general defect in cell polarity or proliferation arrest. Instead, the inhibitors appeared to be initiating a nascent branching program that is reminiscent of when TGFβ-family signaling is impaired.

FIG. 9A: MCF10A-5E cells stably expressing shRUNX1 or shGFP control were grown in 3D culture for 10-11 days with the indicated compounds and imaged by Brightfield microscopy. The total number of multiacini per chamber was counted and scaled to the shGFP DMSO control. Data are shown as the mean±SEM of eight independent cultures.

Figure 9B:
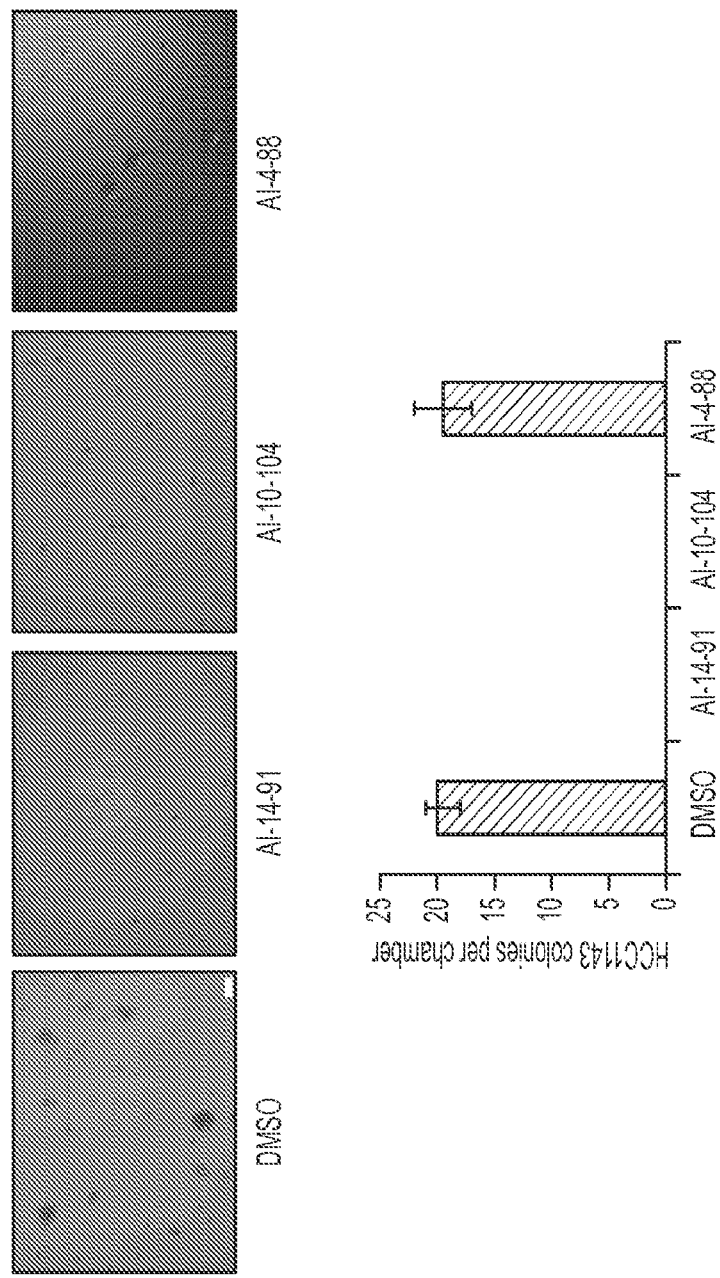
FIG. 9B. Brightfield microscopy images of 3D cultures of HCC1143 cells treated with Al-14-91, Al-10-104, and Al-4-88 and total number of proliferating colonies per chamber.

FIG. 9B: HCC1143 is a cell line of the Basal A subtype with high expression of RUNX transcripts as measured by microarray. HCC1143 cells were grown in 3D culture for 18 days with the indicated inhibitor compounds and imaged by Brightfield microscopy. The total number of proliferating colonies per chamber was counted, and data are shown as the mean±SEM of four independent cultures. Scale bar is 200 μm. A striking blockade in cell survival was observed, with zero detectable colonies after 18 days. These results indicate that persistent RUNX-mediated gene expression is required in a subset of basal-like breast cancers, and CBFβ inhibitors can be used to prevent and/or treat such cancers.

Example 8—Effects of Compounds on Lung Cancer Cells and Normal Lung Cells

Activity of Al-10-104 was tested using several lung cancer cell lines and one immortalized, non-transformed lung cell line. While growth inhibition (assessed by MTT assay) was observed for all cancer cell lines, the potency of inhibition varied. Data for the squamous cell carcinoma of the lung cell line H520 and the immortalized normal lung epithelial cell line BEAS-2B are shown in FIG. 10.

H520 cells were cultured in RPMI 1640 medium, supplemented with fetal bovine serum (10% final concentration), Hepes (1%), and sodium priruvate (1%). The MTT assay used 4×10 5/ml cells. BEAS-2B cells were cultured in DMEM medium with fetal bovine serum (10% final concentration). The MTT assay for the BEAS-2B cell line was performed using 3.5×10 5/ml cells.

At 10 μM dose shown, there was no effect of Al-10-104 on BEAS-2B cell growth after 72 hrs, whereas the H520 cells were inhibited almost as effectively as 1 μM staurosporine (a wide spectrum kinase inhibitor). Al-4-88 was tested as a control, which has a very similar structure to Al-10-104 but lacks a critical functional group which makes it inactive as an inhibitor of RUNX-CBFβ binding. Al-4-88 had no effect on either cell line.

Figure 10:
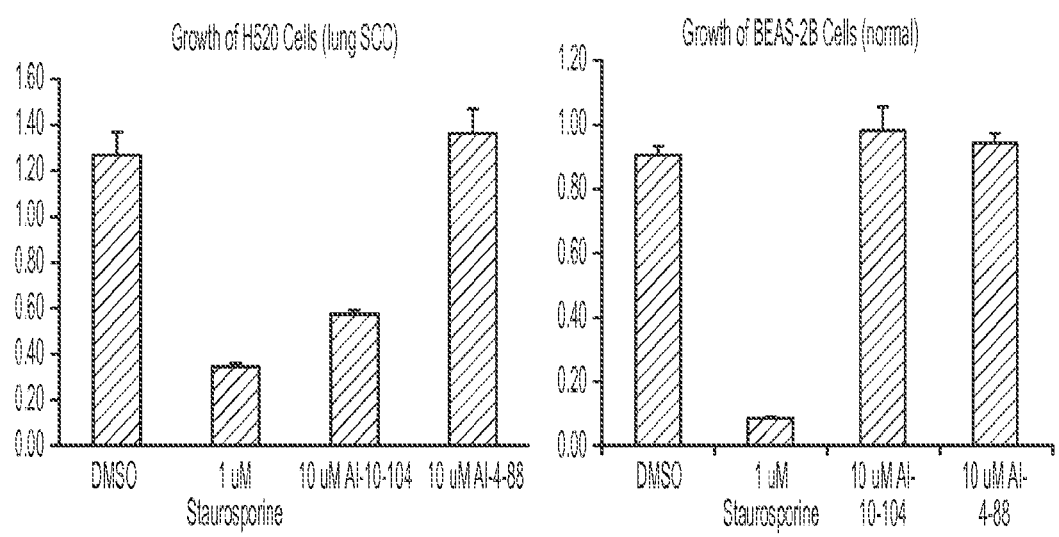
FIG. 10. Effects of Al-10-104 and Al-4-88 on the growth of H520 (lung cancer cells) and BEAS-2B (normal lung cells) measured by MTT assay.

FIG. 10 demonstrates the effects of compounds Al-10-104 and AL-4-88 on the growth of H520 lung cancer cells (left graph) and BEAS-2B normal lung cells (normal control; right graph) measured using the MTT assay, relative to the effects of DMSO and staurosporine.

Figure 11:
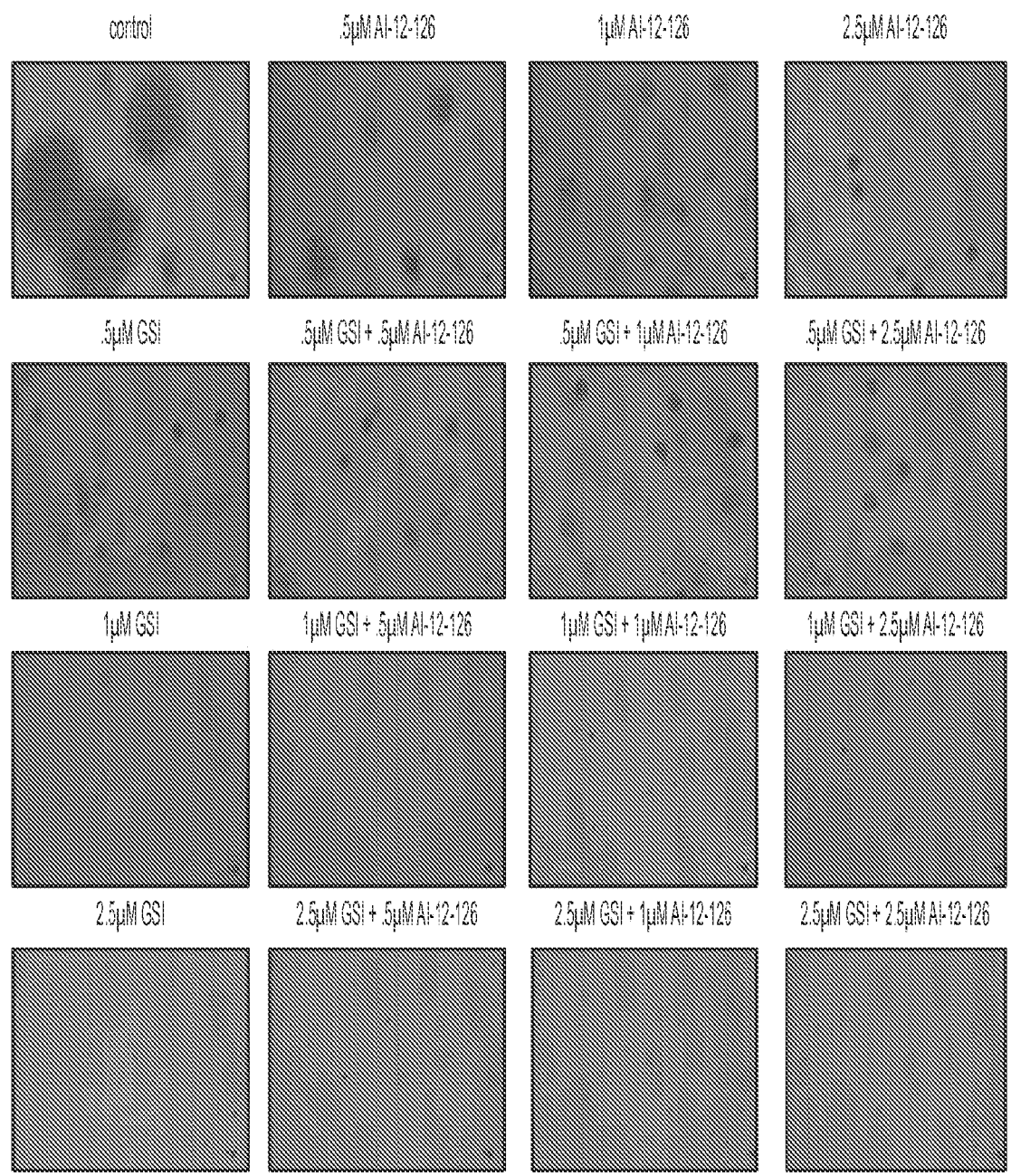
FIG. 11. Effects of Al-12-126 on the colony formation of H460 (lung cancer) cell line.

FIG. 11 shows results of the dose-response effects of Al-12-126 on colony formation of H460 lung cancer cells (16 panels of photomicrographs).

Example 9—Effects of Al-12-126 on Ovarian Cancer Cells

Figure 12:
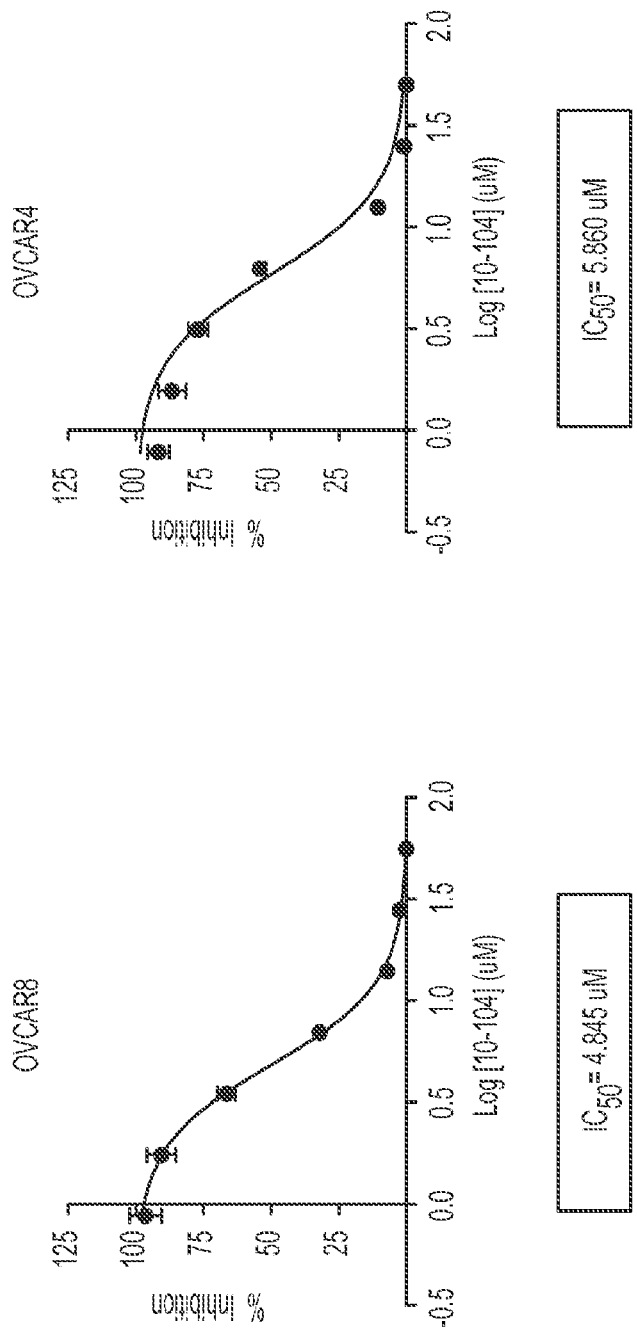
FIG. 12. Effects of Al-10-104 on viability of two ovarian cancer cell lines (OVCAR8 and OVCAR4) assessed by CellTiterGlo.

FIG. 12 demonstrates the effect of Al-10-104 on the viability of two ovarian cancer cell lines (OVCAR8—left graph and OVCAR4—right graph).

OVCAR8 cells were grown in RPMI 1640 supplemented with 10% Fetal bovine serum and 1% antibiotics. OVCAR4 cells were grown in RPMI 1640 supplemented with 20% fetal bovine serum and 1% antibiotics. Cells growing at approximately 70% confluency were trypsinized and 2500 cells per well were re-plated in opaque bottomed 96-well plates.

24 hours after plating, chemical compounds diluted in DMSO were mixed with cell growth media and added to cells. Compounds mixed with media were made at 10× concentration. Final chemical compound concentration is indicated in figures. Cells treated with compounds were incubated for 72 hours in a humidified incubator at 37° C. supplemented with 5% CO2. Percentage of cells viable after 72 hours was determined by CellTitler-Glo according to the manufacturer's instructions. Data analysis was performed using GraphPad 5.0.

Compound Al-10-104 had an $IC_{50}$ of 4.845 μM on OVCAR8 ovarian cancer cells and 5.860 μM on OVCAR4 ovarian cancer cells, as assessed by CellTiter-Glo viability assay. In the graph, the ordinate represents % inhibition and the abscissa represents the log value of the concentration of the compound.

The claimed invention is:
1. A compound of formula (I):

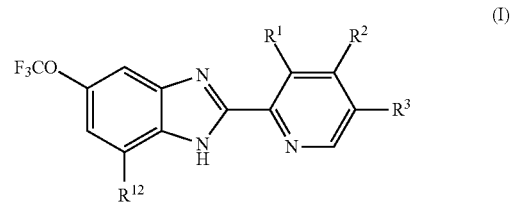

wherein
$R^1$ is selected from H, $C_1$-$C_4$ alkoxy, $NR^4R^5$, or $R^6$, $R^2$ and $R^3$ are independently selected from H, unsubstituted $C_1$-$C_4$ alkoxy, $CO_2H$, $NR^4R^5$, or $OR^6$
wherein $R^6$ is a group of formula (II), (IIIa), (IIIb), (IIIc), (IIId), (IIIe), or (IIIf):

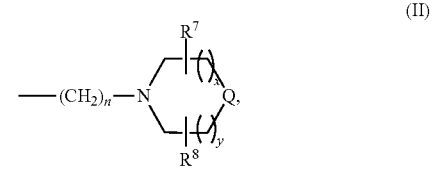

(IIIb) 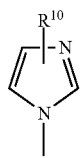

(IIIc) 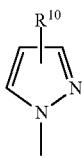

(IIId) 

(IIIe) 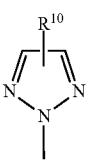

(IIIf) 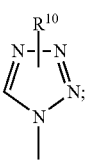

and at least one of $R^1$, $R^2$ and $R^3$ is not H;

$R^4$ and $R^5$ are each independently H or $C_1$-$C_3$ alkyl, or together with the nitrogen carrying them form a pyrrolidine or a piperidine ring;

n ranges from 1-3;

x is 0, 1 or 2;

y is 0, 1 or 2;

Q is O or N—$R^9$, and the sum of x+y≥1, or Q is a bond and the sum x+y≥2;

$R^9$ is $C_1$-$C_3$ alkyl, benzyl, —C(O)phenyl, or a $(CH_2)_n R^{11}$, wherein $R^{11}$ is a group of formula (IVa), (IVb), (IVc), (IVd), (IVe), or (IVf)

(IVa) 

(IVb) 

(IVc) 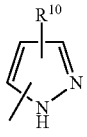

(IVd) 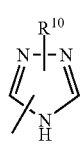

(IVe) 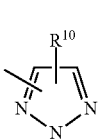

(IVf) 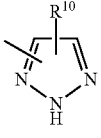

$R^7$ and $R^8$ are each independently H, methyl or ethyl;

$R^{10}$ is H, methyl, ethyl, phenyl or $CO_2H$; and $R^{12}$ is H or $(CH_2)_n$—$CO_2H$;

or a pharmaceutically acceptable salt thereof.

2. A compound of claim 1, wherein
$R^1$ is selected from H, methoxy, ethoxy, $NR^4R^5$, or $OR^6$,
$R^2$ and $R^3$ are independently selected from H, methoxy, ethoxy, $CO_2H$, $NR^4R^5$, or $OR^6$ wherein $R^6$ is a group of formula (II) or a group of formula (IIIe), and at least one of $R^1$, $R^2$ and $R^3$ is not H;
$R^4$ and $R^5$ are each independently methyl or ethyl, or together with the nitrogen carrying them form a pyrrolidine or a piperidine ring;
n ranges from 1-3;
x is 1 or 2;
y is 1 or 2;
Q is O or N—$R^9$;
$R^9$ is benzyl or $(CH_2)_n R^{11}$, wherein $R^{11}$ is a group of formula (IVd);
$R^7$ and $R^8$ are both H;
$R^{19}$ is methyl, phenyl or $CO_2H$; and
$R^{12}$ is H or $(CH_2)_n$—$CO_2H$;
or a pharmaceutically acceptable salt thereof.

3. A compound of claim 2, wherein
$R^1$ is selected from H, methoxy, $NR^4R^5$, or $OR^6$, and $R^3$ is selected from H, methoxy, $CO_2H$, $NR^4R^5$, or $OR^6$, wherein $R^6$ is a group of formula (II);
$R^2$ is H;
$R^4$ and $R^5$ are each independently methyl or ethyl, or together with the nitrogen carrying them form a pyrrolidine or a piperidine ring;
n is 2;
x is 1;
y is 1;
Q is O or N—$R^9$;
$R^9$ is benzyl;
$R^7$ and $R^8$ are both H; and
$R^{12}$ is H;
or a pharmaceutically acceptable salt thereof.

4. A compound of claim 3, wherein $R^1$ is H, $OCH_3$ or a group of formula (II), $R^2$ is H or $OCH_3$, and $R^3$ is H, $OCH_3$ or a group of formula (II); at least one of $R^1$, $R^2$ and $R^3$ is not H; and $R^1$ and $R^3$ are not both a group of formula (II).
5. A compound of claim 4, wherein $R^2$ is H.
6. A compound of claim 5, wherein $R^1$ is H or $OCH_3$.
7. A compound of claim 1, wherein the compound of formula (I) is selected from the group consisting of
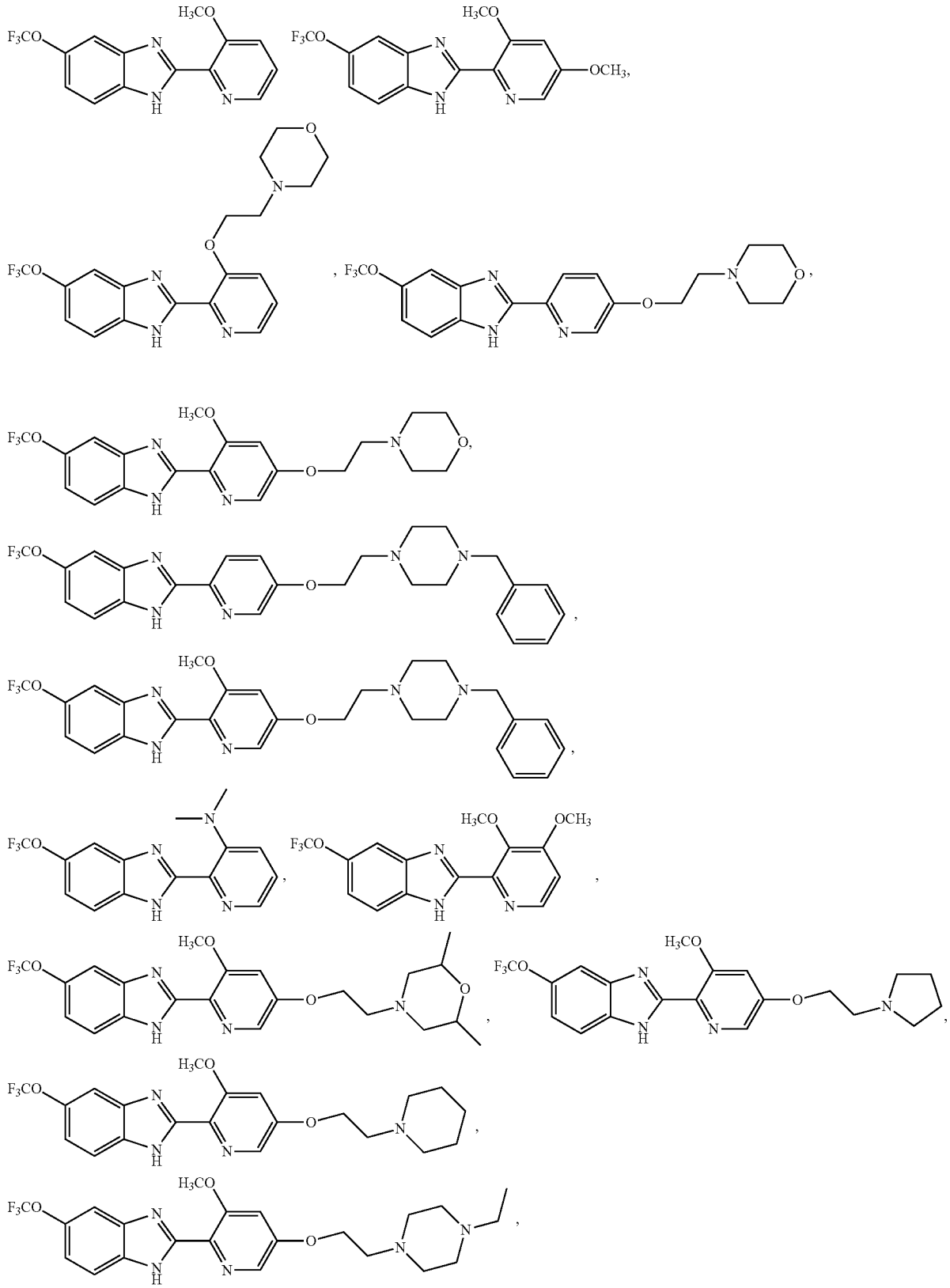

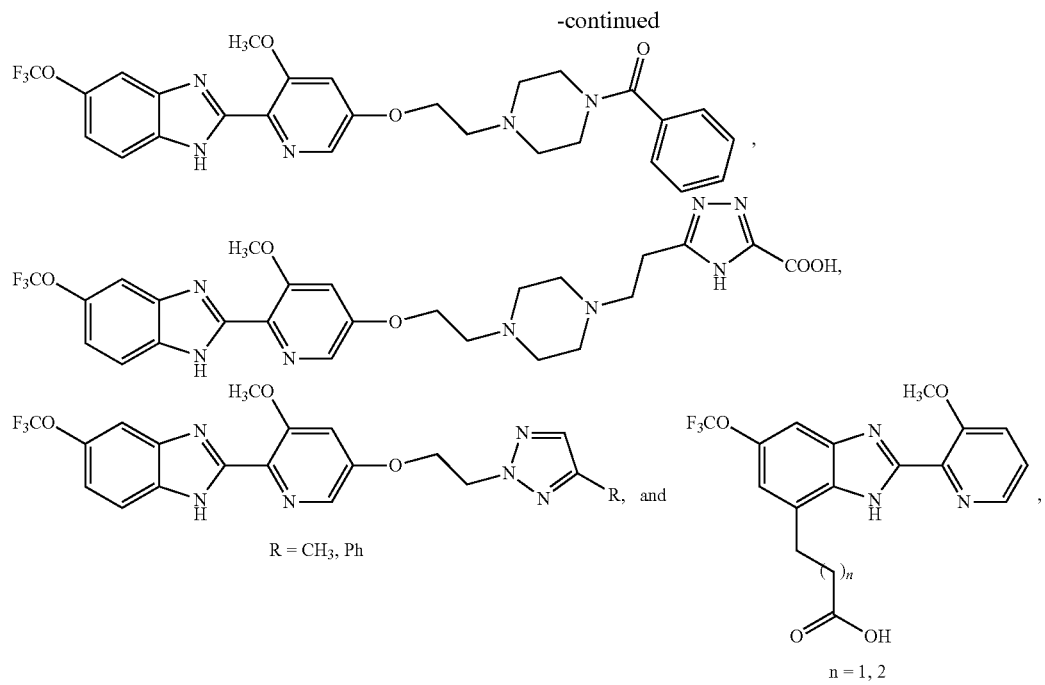

or a pharmaceutically acceptable salt thereof.

8. An acid addition salt of a compound of any one of claim 1.

9. An acid addition salt of claim 8, wherein the salt is a hydrochloride salt.

10. A pharmaceutical composition comprising a compound of claim 1 and a pharmaceutically acceptable carrier.

11. The pharmaceutical composition of claim 10, wherein the composition further comprises a solubilizing agent.

12. The pharmaceutical composition of claim 11, wherein the solubilizing agent is a polyanionic variably substituted sulfobutyl ether of β-cyclodextrin.

13. A method of treating a RUNX-signaling-dependent cancer that expresses wild-type CBFβ in a subject in need thereof, comprising administering to the subject a therapeutically effective amount of a compound of claim 1; wherein the cancer is selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and adenocarcinoma, or mixtures thereof.

14. A method of treating a RUNX-signaling-dependent cancer that expresses wild-type CBFβ in a subject in need thereof, comprising administering to the subject the pharmaceutical composition of claim 10; wherein the cancer is selected from the group consisting of a RUNX-signaling-dependent leukemia that expresses wild-type CBFβ, lung cancer, bladder cancer, ovarian cancer, uterine cancer, endometrial cancer, breast cancer, liver cancer, pancreatic cancer, stomach cancer, cervical cancer, lymphoma, leukemia, acute myeloid leukemia, acute lymphocytic leukemia, salivary gland cancer, bone cancer, brain cancer, colon cancer, rectal cancer, colorectal cancer, kidney cancer, skin cancer, melanoma, squamous cell carcinoma of the tongue, pleomorphic adenoma, hepatocellular carcinoma, pancreatic cancer, squamous cell carcinoma, and adenocarcinoma, or mixtures thereof.

15. An acid addition salt of a compound of claim 7.

16. An acid addition salt of claim 15, wherein the salt is a hydrochloride salt.

17. A pharmaceutical composition comprising a compound of claim 7 and a pharmaceutically acceptable carrier.

18. The pharmaceutical composition of claim 17, wherein the composition further comprises a solubilizing agent.

* * * * *